US006572830B1

(12) United States Patent
Burdon et al.

(10) Patent No.: US 6,572,830 B1
(45) Date of Patent: Jun. 3, 2003

(54) INTEGRATED MULTILAYERED MICROFLUDIC DEVICES AND METHODS FOR MAKING THE SAME

(75) Inventors: Jeremy W. Burdon, Scottsdale, AZ (US); Rong-Fong Huang, Tempe, AZ (US); David Wilcox, Albuquerque, NM (US); Nicholas J. Naclerio, Barrington, IL (US); Cynthia Ann Gorsuch Briscoe, Tempe, AZ (US); Piotr Grodzinski, Chandler, AZ (US); Huinan Yu, Chandler, AZ (US); Robert Marrero, Chandler, AZ (US); Sean Ross Gallagher, Scottsdale, AZ (US); Yuk-Tong Chan, Scottsdale, AZ (US); Barbara McNeil Foley, Phoenix, AZ (US); Xunhu Dai, Gilbert, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/337,086

(22) Filed: Jun. 21, 1999

Related U.S. Application Data

(63) Continuation-in-part of application No. 09/235,081, filed on Jan. 21, 1999.
(60) Provisional application No. 60/103,701, filed on Oct. 9, 1998.

(51) Int. Cl.[7] .................... B01J 10/00; B01J 19/12; H05B 6/64; H05B 6/80
(52) U.S. Cl. ............... 422/186.29; 422/129; 422/186; 422/240; 156/89.11; 156/89.12; 219/678; 219/687; 219/756
(58) Field of Search .................. 422/129, 186, 422/186.29, 240; 156/89.11, 89.12; 219/678, 687, 756

(56) References Cited

U.S. PATENT DOCUMENTS

| 3,293,072 A | 12/1966 | Doolittle et al. ............ 428/430 |
| 3,506,473 A | 4/1970 | Ettre et al. .................. 427/210 |
| 3,574,029 A | 4/1971 | Ettre et al. .................. 156/231 |
| 3,598,679 A | 8/1971 | Ettre et al. .................. 156/249 |
| 3,948,706 A | 4/1976 | Schmeckenbecher |
| 3,956,052 A | 5/1976 | Koste et al. |

(List continued on next page.)

FOREIGN PATENT DOCUMENTS

| DE | 197 25 948 A1 | 12/1998 |
| EP | 0313090 | 4/1989 |

(List continued on next page.)

OTHER PUBLICATIONS

M.R. Gongora–Rubio et al. "Overview of low temperature co–fired ceramics tape technology for meso–system technology (MsST)" Sensor and Actuators A, 89, pp. 222–241, 2001.*

Ghandi, "VLSI Fabrication Principles", Wiley, Ch. 10 (1983).

(List continued on next page.)

Primary Examiner—Jill Warden
Assistant Examiner—John S. Starsiak, Jr.

(57) ABSTRACT

A multilayered microfluidic device having a substantially monolithic structure is formed by sintering together a plurality of green-sheet layers. The substantially monolithic structure has an inlet port for receiving fluid, an outlet port for releasing fluid, and an interconnection between the inlet port and the outlet port. The substantially monolithic structure may also include a variety of components to enable useful interaction with the fluid, such as electrically conductive pathways, heaters, fluid sensors, fluid motion transducers, and optically transmissive portions. The components are preferably fabricated using thick-film or green-sheet technology and are preferably co-fired with and sintered to the green-sheet layers to become integral with the substantially monolithic structure.

13 Claims, 14 Drawing Sheets

U.S. PATENT DOCUMENTS

| | | |
|---|---|---|
| 3,991,029 A | 11/1976 | Adelman .................... 524/555 |
| 4,035,613 A | 7/1977 | Sagawa et al. |
| 4,118,237 A | 10/1978 | Beall et al. ..................... 501/3 |
| 4,523,121 A | 6/1985 | Takahashi et al. .......... 310/334 |
| 4,551,357 A | 11/1985 | Takeuchi |
| 4,610,741 A | 9/1986 | Mase et al. .............. 156/89.15 |
| 4,674,325 A | 6/1987 | Kiyobe et al. |
| 4,737,208 A | 4/1988 | Bloechle et al. ............... 156/90 |
| 4,806,295 A | 2/1989 | Trickett et al. .......... 156/89.22 |
| 4,833,000 A | 5/1989 | Trickett et al. ............. 428/137 |
| 4,929,295 A | 5/1990 | Kohno et al. ............... 156/230 |
| 4,939,021 A | 7/1990 | Aoki et al. |
| 4,985,098 A | 1/1991 | Kohno et al. ............ 156/89.16 |
| 4,991,283 A | 2/1991 | Johnson et al. ............... 29/595 |
| 5,008,151 A | 4/1991 | Tominaga et al. .......... 428/343 |
| 5,089,071 A | 2/1992 | Tominaga et al. |
| 5,174,842 A | 12/1992 | Hamuro et al. .......... 156/89.12 |
| 5,176,771 A | 1/1993 | Bravo et al. .................. 156/85 |
| 5,254,191 A | 10/1993 | Mikeska et al. ......... 156/89.15 |
| 5,261,986 A | 11/1993 | Kawabata et al. |
| 5,265,327 A | 11/1993 | Faris et al. .................... 29/825 |
| 5,271,150 A | 12/1993 | Inasaka ....................... 29/852 |
| 5,304,487 A | 4/1994 | Wilding et al. |
| 5,312,674 A | 5/1994 | Haertling et al. ........... 428/210 |
| 5,358,593 A | 10/1994 | Hamuro et al. ............. 156/378 |
| 5,435,875 A | 7/1995 | Saitoh et al. ................ 156/245 |
| 5,478,420 A | 12/1995 | Gauci et al. ............. 156/89.17 |
| 5,480,614 A | 1/1996 | Kamahori .................... 422/70 |
| 5,534,092 A | 7/1996 | Ogawa et al. |
| 5,534,328 A | 7/1996 | Ashmead et al. ........... 428/166 |
| 5,538,582 A | 7/1996 | Natarajan et al. ........... 156/285 |
| 5,540,884 A | 7/1996 | Chiao .......................... 419/47 |
| 5,565,729 A | 10/1996 | Faris et al. .......... 313/103 CM |
| 5,585,069 A | 12/1996 | Zanzucchi et al. .......... 422/100 |
| 5,587,128 A | * 12/1996 | Wilding et al. ................ 422/50 |
| 5,595,712 A | 1/1997 | Harbster et al. ............. 422/129 |
| 5,601,673 A | 2/1997 | Alexander ............... 156/89.12 |
| 5,603,351 A | 2/1997 | Cherukuri et al. .......... 137/597 |
| 5,607,535 A | 3/1997 | Tsukada et al. ............. 156/252 |
| 5,611,214 A | 3/1997 | Wegeng et al. ............... 62/498 |
| 5,614,053 A | 3/1997 | Toudo et al. ................ 156/312 |
| 5,632,876 A | 5/1997 | Zanzucchi et al. .......... 204/600 |
| 5,639,508 A | 6/1997 | Okawa et al. ............... 427/100 |
| 5,676,788 A | 10/1997 | Natarajan et al. ........... 156/285 |
| 5,681,410 A | 10/1997 | Takeuchi et al. ......... 156/89.15 |
| 5,683,535 A | 11/1997 | Karr ........................... 156/285 |
| 5,707,476 A | 1/1998 | Bezama et al. ............. 156/285 |
| 5,728,244 A | 3/1998 | Nanataki et al. |
| 5,746,874 A | 5/1998 | Natarajan et al. ........... 156/285 |
| 5,753,060 A | 5/1998 | Mori ........................... 156/264 |
| 5,759,320 A | 6/1998 | Natarajan et al. ........... 156/228 |
| 5,779,833 A | 7/1998 | Cawley et al. ........... 156/89.11 |
| 5,785,800 A | 7/1998 | Natarajan et al. ........... 156/382 |
| 5,792,379 A | 8/1998 | Dai et al. ............. 252/62.9 PZ |
| 5,795,545 A | 8/1998 | Koripella et al. ............. 422/94 |
| 5,811,062 A | 9/1998 | Wegeng et al. .............. 422/129 |
| 5,821,181 A | 10/1998 | Bethke et al. .................. 501/8 |
| 5,842,106 A | 11/1998 | Thaler et al. ................... 419/8 |
| 5,855,803 A | 1/1999 | Bailey et al. ................ 216/56 |
| 5,858,193 A | 1/1999 | Zanzucchi et al. .......... 204/601 |
| 5,858,195 A | 1/1999 | Ramsey ..................... 204/601 |
| 5,863,708 A | 1/1999 | Zanzucchi et al. .......... 430/320 |
| 5,906,723 A | 5/1999 | Mathies et al. |
| 5,922,591 A | 7/1999 | Anderson et al. |
| 5,939,291 A | 8/1999 | Loewy et al. .............. 435/91.2 |
| 5,939,312 A | 8/1999 | Baier et al. |
| 5,958,694 A | 9/1999 | Nikiforov et al. |
| 5,961,930 A | * 10/1999 | Chatterjee et al. .......... 422/130 |
| 5,961,932 A | 10/1999 | Ghosh et al. ............... 422/193 |
| 5,965,092 A | 10/1999 | Chatterjee et al. .......... 422/130 |
| 5,971,355 A | 10/1999 | Biegelsen et al. ........... 251/129 |
| 5,976,472 A | 11/1999 | Chatterjee et al. .......... 422/130 |
| 5,985,119 A | 11/1999 | Zanzucchi et al. .......... 204/450 |
| 5,993,750 A | 11/1999 | Ghosh et al. ............... 422/191 |

FOREIGN PATENT DOCUMENTS

| | | |
|---|---|---|
| EP | 0 649 008 A2 | 10/1994 |
| EP | 0 744 389 A1 | 11/1996 |
| EP | 0 870 541 A2 | 10/1998 |
| EP | 0 870 541 A2 3 | 10/1998 |
| JP | 53-49264 A | 5/1978 |
| JP | 61-288154 | 12/1986 |
| JP | 63-42147 A | 2/1988 |
| JP | 2-117117 A | 5/1990 |
| JP | 2-166793 | 6/1990 |
| JP | 2-129603 A | 9/1990 |
| JP | 3-148196 A | 6/1991 |
| JP | 4-18795 A | 1/1992 |
| JP | 4-114961 | 4/1992 |
| JP | 5-267844 A | 10/1993 |
| JP | 6-104572 A | 4/1994 |
| JP | 6-152135 A | 5/1994 |
| JP | 6-290987 A | 10/1994 |
| JP | 7-289886 | 11/1995 |
| JP | 8-108422 A | 4/1996 |
| JP | 8-267421 A | 10/1996 |
| JP | 63-239999 | 10/1998 |
| WO | WO 98/50154 | 11/1998 |
| WO | WO 00/21659 | 4/2000 |
| WO | WO 01/35484 | * 5/2001 |

OTHER PUBLICATIONS

Gonora–Rubio et al., "Overview of low temperature co–fired ceramics tape technology for meso–system technology (MsST)", Sensors and Actuators A:Physical, vol. 89, Issue 3, pp. 222–241 (2001).

Ibrahim et al., "Real–time microchip PCR for detecting single–base differences in viral and human DNA", Anal. Chem., 70(9):2013–2017 (1998).

Shoffner et al., "Chip PCR. I. Surface passivation of microfabricated silicon–glass chips for PCT", Nucl. Acids. Res. 24:375–379 (1996).

Morton L. Topfer, "Chapter 3:Technology" Thick–Film Microelectronics, pp. 40–59 (1977).

Microsphere Selection Guide, Bangs Laboratories, Inc. Product Information Bulletin. Mar., 1999.

Bangs, L. B., The Latex Course (Apr. 1996), Immunological Applicaitons of Microspheres.

Belgrader P. et al., "Rapid pathogen detection using a microchip PCT array instrument", *Clinical Chemistry*, vol. 44, No. 10, pp 2191–2194, (1998).

Espinoza–Vallejos, P. et al., "Meso (Intermediate)–Scale electromechanical systems for the measurement and control of sagging in LTCC structures", Med. Res. Soc. Symp. Pros., vol. 518, pp. 73–79 (1998).

Fuhr, G. et al., "Pumping of water solutions in microfabricated electrohydrodynamic systems" Part of the conference on Micro Electro Mechanical Systems, pp. 25–30 (1992).

Gongora–Rubio, M. et al. "The utilization of low temperature co0fired ceramics (LTCC–ML) technology for meso–scale EMS, a simple thermistor based flow sensor", Sensors and Actuators, vol. 73, pp. 215–221 (1999).

Gongora–Rubio, M. et al., "A Meso–scale Electro–magnetically actuated normally closed valve realized on LTCC tapes", Part of the SPIE Conference on Microfluidic Devices and Systems II, Sep. 1999, SPIE, vol. 3877, pp. 230–239.

Gongora–Rubio, M. et al., "A simple thermistor based flow sensor using the LTCC–ML technology", Quimica Analitica, vol. 18, pp. 30–32 (1999).

Gui, Z. et al., Influence of additives on sintering processing and properties of high performance piezoelectric ceramics, Solic State Phenomina, vol.s 25 & 26, pp. 309–316 (1992).

Kim, M. et al., "The fabrication of flow conduits in ceramic tapes and the measurement of fluid flow through these conduits" DSC–vol. 66, Micro–Electro–Mechanical Systems (MEMS) –pp. 171–177 (1998).

Kricka, Larry J., "Revolution on a square centimeter" Nature Biotechnology, vol. 16, pp. 513–514 (1998).

Liu, J. H. et al., "Study of thick–film pH sensors" Sensors and Actuatoors $B_1$, vol. 13–14, pp. 566–567 (1993).

Manz, Andreas, "Electroosmotic pumping and electrophoretic separations for miniaturized chemical analysis systems" J. Micromech. Microeng., vol. 4, pp. 257–265, (1994).

Mistler, Richard E., "Tape Casting: The Basic Process for Meeting the Needs of the Electronics Industry" Ceramic Bulletin, vol. 69, No. 6, pp. 1022–1026, (1990).

Provamce, J.D. "Performance Review of Thick Film Materials" reprinted from Insulation Circuits (Apr. 1977).

Santiago–Avilés, J. J. et al., "The utilization of low temperature co–fired ceramic tapes for 3 dimensional meso–scale fabrication" Química Analítica, vol. 18, [Suppl 1]: pp. 33–34 (1999).

Sinclair, Bob "To Bead or Not to Bead: Applications of Magnetic Bead Technology" The Scientist, pp. 16–19, Jun. 22 (1998).

Waters, Larry C. et al., "Microchip Device for Cell Lysis, Multiplex PCR Amplification, and Electrophoretic Sizing" Analytical Chemistry, vol. 70, No. 1, pp. 158–162 (1998).

* cited by examiner

INTEGRATED MULTILAYERED MICROFLUDIC DEVICES AND METHODS FOR MAKING THE SAME

CROSS-REFERENCE TO RELATED APPLICATIONS

This application is a continuation-in-part of U.S. application Ser. No. 09/235,081, filed on Jan. 21, 1999, which, in turn, claims the benefit of U.S. Provisional Application No. 60/103,701, filed Oct. 9, 1998.

BACKGROUND OF THE INVENTION

1. Field of the Invention

This invention relates to the field of microfluidic devices. More particularly, this invention relates to a multilayered microfluidic device, formed from layers of greensheet, having components that are co-fired with and sintered to the green-sheet layers to provide an integrated and monolithic structure and also relates to methods for making such devices.

2. Description of Related Art

Microfluidic devices have a wide variety of chemical and biological applications. Specifically, microfluidic devices can be used to mix, react, meter, analyze, and detect chemicals and biological materials in a fluid state. Many synthetic and analytical techniques that conventionally require large, bulky, and complicated apparatus can be miniaturized as microfluidic devices.

Microfluidic devices are most commonly made from silicon, glass, or plastic substrates. However, each of these materials has certain disadvantages that limit its utility. Channels and various other microfluidic structures may be etched into silicon, but such etching processes are not typically able to form the complex three-dimensional structures and embedded structures that are often desirable in microfluidic devices. Silicon, as a material, is also not compatible with many fluids containing biological materials. Typically, this problem is overcome by the additional step of applying a special coating to the microfluidic channels. Finally, because silicon is a semiconductor, certain pumping techniques, such as electrohydrodynamic pumping and electroosmotic pumping, are difficult or impossible to achieve. Overall, silicon is an expensive substrate to work with, making it of only limited use for the large scale production of microfluidic devices that typically do not require structures with dimensions less than about 10 microns.

Like silicon, channels may also be etched into glass substrates. Although three-dimensional and embedded structures can be built up by bonding together successive layers of glass, using an anodic bonding process, this bonding process is difficult and very costly. In particular, each layer is added sequentially, i.e., only one at a time. Moreover, the surface of each successive layer must be nearly perfectly flat in order to achieve reliable bonding. This stringent flatness requirement makes the fabrication of multilayered glass devices difficult and expensive and results in low yields.

Plastic also has a number of disadvantages as a substrate for microfluidic devices. First, most types of plastic substrate cannot be used above about 350° C., thereby limiting the extent to which plastic microfluidic devices can heat fluids. Second, many plastic materials, like silicon, have biocompatibility problems. Accordingly, biocompatibility is typically achieved by the additional step of adding special coatings to the fluid passageways. Third, it is believed that, like silicon, electroosmotic pumping would be difficult or impossible to achieve in plastic microfluidic devices because of the lack of available fixed surface charge. Fourth, the ability to fabricate three-dimensional and embedded structures in plastic devices is limited because it is be difficult to join more than two plastic layers together.

SUMMARY OF THE INVENTION

In a first principal aspect, the present invention provides a multilayered microfluidic device comprising a substantially monolithic structure formed from a plurality of green-sheet layers sintered together, wherein the green-sheet layers include particles selected from the group consisting of ceramic particles, glass particles, and glass-ceramic particles. The substantially monolithic structure has a fluid passageway defined therein. The fluid passageway has an inlet port for receiving fluid, an outlet port for releasing a fluid, and an interconnection between the inlet port and the outlet port. The substantially monolithic structure also has an electrically conductive pathway defined therein, at least a portion of which is formed by sintering a thick-film paste to at least one of the green-sheet layers.

In a second principal aspect, the present invention provides a multilayered microfluidic device comprising a substantially monolithic structure formed from a plurality of green-sheet layers sintered together, wherein the green-sheet layers include particles selected from the group consisting of ceramic particles, glass particles, and glass-ceramic particles. The substantially monolithic structure has a fluid passageway defined therein. The fluid passageway has an inlet port for receiving fluid, an outlet port for releasing a fluid, and an interconnection between the inlet port and the outlet port. A fluid sensor for sensing fluid in a portion of the fluid passageway is sintered to at least one of the green-sheet layers so as to be integral with the substantially monolithic structure.

In a third principal aspect, the present invention provides a multilayered microfluidic device comprising a substantially monolithic structure formed from a plurality of green-sheet layers sintered together, wherein the green-sheet layers include particles selected from the group consisting of ceramic particles, glass particles, and glass-ceramic particles. The substantially monolithic structure has a fluid passageway defined therein. The fluid passageway has an inlet port for receiving fluid, an outlet port for releasing a fluid, and an interconnection between the inlet port and the outlet port. A fluid motion transducer for converting electrical energy into fluid motion in a portion of the fluid passageway is sintered to at least one of the green-sheet layers so as to be integral with the substantially monolithic structure.

In a fourth principal aspect, the present invention provides a multilayered microfluidic device comprising a substantially monolithic structure formed from a plurality of green-sheet layers sintered together, wherein the green-sheet layers include particles selected from the group consisting of ceramic particles, glass particles, and glass-ceramic particles. The substantially monolithic structure has a fluid passageway defined therein. The fluid passageway has an inlet port for receiving fluid, an outlet port for releasing a fluid, and an interconnection between the inlet port and the outlet port. The substantially monolithic structure also includes an optically transmissive portion for providing external optical access to a portion of the fluid passageway.

In a fifth principal aspect, the present invention provides a multilayered microfluidic device comprising a substantially monolithic structure formed from a plurality of greensheet layers sintered together, wherein the green-sheet layers include particles selected from the group consisting of ceramic particles, glass particles, and glass-ceramic particles. The substantially monolithic structure has a fluid passageway defined therein. The fluid passageway has an inlet port for receiving fluid, an outlet port for releasing a fluid, an interconnection between the inlet port and the outlet port, and includes a cavity. The substantially monolithic structure also includes means for lysing. cells in the cavity.

In a sixth principal aspect, the present invention provides a method for making a multilayered microfluidic device. A plurality of green-sheet layers is textured in a first predetermined pattern defining a fluid passageway. The green-sheet layers include particles selected from the group consisting of ceramic particles, glass particles, and glass-ceramic particles. A thick-film paste is applied to the green-sheet layers in a second predetermined pattern defining a fluid-interacting component. The green-sheet layers are then sintered together at a predetermined temperature for a predetermined amount of time to form a substantially monolithic structure. The substantially monolithic structure has the fluid passageway and the fluid-interacting component defined therein.

In a seventh principal aspect, the present invention provides a multilayered microfluidic device comprising a substantially monolithic structure formed from a plurality of green-sheet layers sintered together, wherein the green-sheet layers include particles selected from the group consisting of ceramic particles, glass particles, and glass-ceramic particles. The substantially monolithic structure has a fluid passageway defined therein. Disposed within the fluid passageway is a hydrophobic region sintered to one of the green-sheet layers.

Because the multilayered microfluidic devices of the present invention are made from a plurality of green-sheet layers sintered together, the devices may be provided with a wide variety of properties and functionalities useful for chemical and biological applications. The materials of the green-sheet layers may be chosen so as to be chemically and biologically compatible with the fluids used in the device and may also be chosen to be compatible with the particular range of temperature used in the device.

Additionally, the green-sheet layers in the device need not be all made of the same material. In this way, the device may be advantageously provided with different properties, such as thermal conductivity, in different locations. As an important example, one of the green-sheet layers may include glass particles, so as to provide an optically transmissive layer allowing external optical access to portions of the fluid passageways in the device.

By allowing each green-sheet layer to be processed individually before being sintered together, complicated structures may also be built into the devices of the present invention. For example, the fluid passageway in the device may be defined by structures, such as vias and channels, which are formed into several green-sheet layers before the layers are sintered together. Accordingly, the fabrication out of a plurality of layers allows the fluid passageway to have a complicated three-dimensional structure that would otherwise be difficult to achieve.

Green-sheet technology also allows the provision into the devices of a wide variety of functional components, such as heating elements, cooling elements, fluid sensors, and fluid motion transducers. Advantageously, these functional components may be co-fired with and sintered to the green-sheet layers so as to be integral with the device. Such integral components are more efficiently and reliably incorporated into the device, and, thus, facilitate large-scale manufacturing of microfluidic devices.

Thick-film technology is an important way of providing such integral components. Thick-film pastes may silk-screened onto individual green-sheet layers and then co-fired with and sintered to the green-sheet layers to become integral with the device. The thick-films may include conductive materials, such as metals, to provide electrically conductive pathways in the device. In particular, the use of conductive traces deposited onto the surfaces of green-sheet layers in combination with conductor-filled vias in the green-sheet layers allows for the efficient fabrication of complicated electrical conduction pathways in the device. Thick-film technology also allows other materials, such as thermoelectric, piezoelectric, and high magnetic permeability materials to be incorporated into the device.

DETAILED DESCRIPTION OF THE INVENTION

A multilayered microfluidic device in accordance with the present invention is made from layers of green-sheet that have been laminated and sintered together to form a substantially monolithic structure. Green-sheet is a composite material that includes inorganic particles of glass, glass-ceramic, ceramic, or mixtures thereof, dispersed in a polymer binder, and may also include additives such as plasticizers and dispersants. The green-sheet is preferably in the form of sheets that are 50 to 250 microns thick. The ceramic particles are typically metal oxides, such as aluminum oxide or zirconium oxide. An example of such a green-sheet that includes glass-ceramic particles is "AX951" that is sold by E. I. Du Pont de Nemours and Company. An example of a green-sheet that includes aluminum oxide particles is "Ferro Alumina" that is sold by Ferro Corp. The composition of the green-sheet may also be custom formulated to meet particular applications.

The green-sheet layers are laminated together and then fired to form a substantially monolithic multilayered structure. The manufacturing, processing, and applications of ceramic green-sheets are described generally in Richard E. Mistler, "Tape Casting: The Basic Process for Meeting the Needs of the Electronics Industry," Ceramic Bulletin, vol. 69, no. 6, pp. 1022–26 (1990), and in U.S. Pat. No. 3,991,029, which are incorporated herein by reference.

Figure 1:
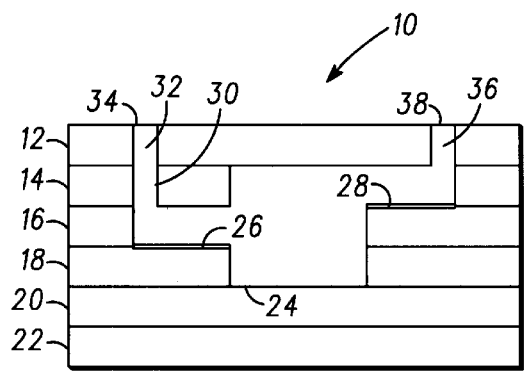
FIG. 1 is a schematic representation of part of a multi-layered microfluidic device, in accordance with an embodiment of the present invention.

Shown in FIG. 1 is a cross-sectional view of a representative multilayered microfluidic device 10. Multilayered microfluidic device 10 is made from green-sheet layers 12–22 that have been laminated and sintered together to form a substantially monolithic structure. Device 10 includes a cavity 24 that is connected to a first channel 26 and to a second channel 28. First channel 26 is also connected to a first via 30 which, in turn, is connected to a second via 32 that defines a first fluid port 34. Second channel 28 is connected to a third via 36 that defines a second fluid port 38. In this way, cavity 24 is in fluid communication with fluid ports 34 and 38. More particularly, vias 32 and 30, first channel 26, cavity 24, second channel 28, and via 36 together define a fluid passageway interconnecting fluid ports 34 and 38. In this configuration, ports 34 and 38 could be used as fluid input or output ports to add reactants and to remove products, with cavity 24 providing a place for reactions.

Figure 1A:
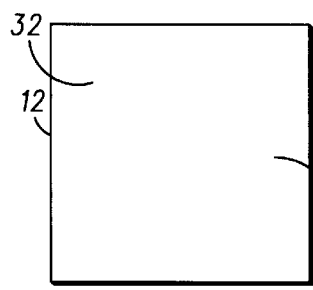
FIGS. 1A–1F are partial views of the multilayered microfluidic device of FIG. 1, with each partial view corresponding to a plan view of a distinct layer of the multilayered microfluidic device of FIG. 1.
Figure 1B:
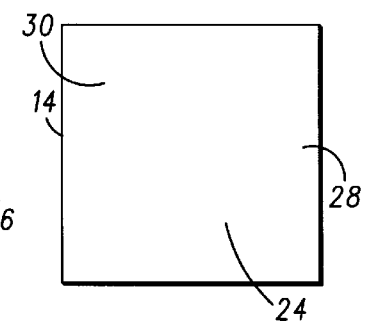
Figure 1C:
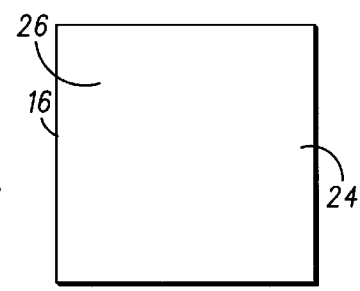
Figure 1D:
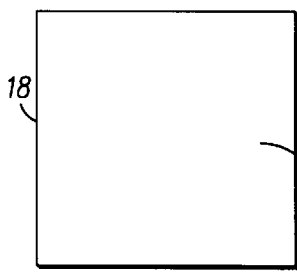
Figure 1E:
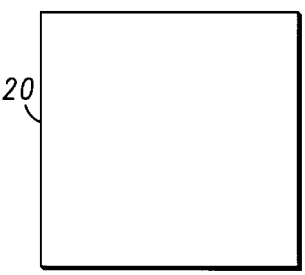
Figure 1F:
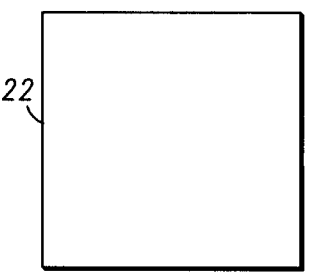

FIGS. 1A–1F are plan views of each one of layers 12–22, individually, to show what portions would be formed into each one the layers 12–22 before lamination to provide the aforementioned fluid passageway. As shown in FIG. 1A, layer 12 has via 32 and via 36. As shown in FIG. 1B, layer 14 has via 30 and has a portion of cavity 24 connected to channel 28. As shown in FIG. 1C, layer 16 has a portion of cavity 24 connected to channel 26. As shown in FIG. 1D has a portion of cavity 24. Layers 20 and 22, shown in FIGS. 1E and 1F, respectively, have no such structures.

The method of fabricating the multilayered microfluidic devices of the present invention begins with providing sheets of green-sheet that are preferably 50 to 250 microns thick. The sheets of green-sheet are cut to the desired size, typically 6 inches by 6 inches for conventional processing. Each green-sheet layer may then be textured using various techniques to form desired structures, such as vias, channels, or cavities, in the finished multilayered structure.

As used herein, the term "via" refers to a hole formed in a green-sheet layer. Typical vias have diameters ranging from 100 to 500 microns. Vias may also be filled in subsequent steps with other materials, such as thick-film pastes.

As used herein, the term "channel" refers to an open region within a multilayered structure that has its length greater than its diameter. Typical channels have diameters ranging from under 100 microns to 500 microns. In the microfluidic devices of the present invention, channels are typically used to transfer fluid materials. "Channels" may also be referred to as "capillaries" or "conduits."

As used herein, the term "cavity" refers to a hole or open area in the microfluidic device. Cavities are typically used to contain, mix, react, or transfer fluid materials. Typically, cavities are connected to a channel or a via to provide input or output of material, and, in such cases, the cavity has dimensions greater than that of the channel or via. "Cavities" may also be referred to as "wells."

Various techniques may be used to texture a green-sheet layer. For example, portions of a green-sheet layer may be punched out to form vias or channels. This operation may be accomplished using conventional multilayer ceramic punches, such as the Pacific Trinetics Corp. Model APS-8718 Automated Punch System. Instead of punching out part of the material, features, such as channels and wells may be embossed into the surface of the green-sheet by pressing the green-sheet against an embossing plate that has a negative image of the desired structure. Texturing may also be accomplished by laser tooling with a laser via system, such as the Pacific Trinetics LVS-3012.

Next, a wide variety of materials may be applied, preferably in the form of thick-film pastes, to each textured green-sheet layer. For example, electrically conductive pathways may be provided by depositing metal-containing thick-film pastes onto the green-sheet layers. Thick-film pastes typically include the desired material, which may be either a metal or a dielectric, in the form of a powder dispersed in an organic vehicle, and the pastes are designed to have the viscosity appropriate for the desired deposition technique, such as screen-printing. The organic vehicle may include resins, solvents, surfactants, and flow-control agents. The thick-film paste may also include a small amount of a flux, such as a glass frit, to facilitate sintering. Thick-film technology is further described in J. D. Provance, "Performance Review of Thick Film Materials," *Insulation/Circuits* (April, 1977) and in Morton L. Topfer, *Thick Film Microelectronics, Fabrication, Design, and Applications* (1977), pp. 41–59, which are incorporated herein by reference.

The porosity of the resulting thick-film can be adjusted by adjusting the amount of organic vehicle present in the thick-film paste. Specifically, the porosity of the thick-film can be increased by increased the percentage of organic vehicle in the thick-film paste. Similarly, the porosity of a green-sheet layer can be increased by increasing the proportion of organic binder. Another way of increasing porosity in thick-films and green-sheet layers is to disperse within the organic vehicle, or the organic binder, another organic phase that is not soluble in the organic vehicle. Polymer microspheres can be used advantageously for this purpose.

To add electrically conductive pathways, the thick film pastes typically include metal particles, such as silver, platinum, palladium, gold, copper, tungsten, nickel, tin, or alloys thereof. Silver pastes are preferred. Examples of suitable silver pastes are silver conductor composition numbers 7025 and 7713 sold by E. I. Du Pont de Nemours and Company.

The thick-film pastes are preferably applied to a green-sheet layer by screen-printing. In the screen-printing process, the thick-film paste is forced through a patterned silk screen so as to be deposited onto the green-sheet layer in a corresponding pattern. Typically, the silk screen pattern is created photographically by exposure to a mask.

In this way, conductive traces may be applied to a surface of a green-sheet layer. Additionally, vias present in the green-sheet layer may be filled with the conductive thick-film paste to provide electrical connections between layers.

In certain applications it also desirable to add glass coatings to the surfaces of green-sheet layers. For example, glass coatings provide smooth walls in fluid passageways, thereby providing better fluid flow and reducing contamination problems. Glass coatings can also serve as barriers between the fluid and green-sheet materials that may be reactive or otherwise incompatible with the fluid.

One way of adding a glass coating is by screen-printing a thick-film paste containing glass particles onto the surface of a green-sheet layer. After lamination, the thick-film paste is then co-fired with the green-sheet layers to form a smooth glass coating sintered to the surface of the green-sheet layer.

Another way to achieve a glass coating is by using a glass-ceramic green-sheet layer and sintering it more aggressively than is typical, i.e., by using a faster temperature increase during the sintering step, a higher final sintering temperature, and a longer sintering time. In particular, the viscosity of the glass phase drops quickly when the temperature is increased above the glass softening point. Consequently, aggressive sintering will tend to drive the glass phase from the interior of the green-sheet layer to its surface, before appreciable crystallization with the ceramic phase. In this way, a glass coating is formed on the surface of the green-sheet layer. Suitable glass-ceramic systems include the T2000 dielectric tape sold by Motorola, Inc. and the glass-ceramic compositions disclosed in U.S. Pat. No. 5,821,181, which is incorporated herein by reference.

For example, the standard sintering parameters for the Motorola T2000 dielectric tape call for ramping the temperature at a rate of about 5° C. per minute to reach a final sintering temperature of about 875° C., which is then maintained for about 30 minutes. However, to achieve a glass coating, the temperature may instead be ramped at a rate of about 7° C. per minute, or, alternatively, the final sintering temperature may be increased to about 925° C.

Of course, another way of achieving smooth glass walls for fluid passageways is to use glass green-sheet layers.

Many other materials may also be added to each green-sheet layer to provide desired functionalities. For example, optical materials may be added to provide optical windows. Piezoelectric materials may also be added to provide piezoelectric members. Thermoelectric materials maybe added to provide thermoelectric elements. High magnetic permeability materials, such as ferrites, may be added, to provide cores for strong electromagnets. Green-sheet materials have a great deal of flexibility to accommodate the addition of dissimilar materials. To ensure that the materials are placed reliably in the finished device, it is preferable that the materials added to the green-sheet layers are able to be co-fired with the green-sheet material, as described below.

After the desired structures are formed in each layer of green-sheet, preferably a layer of adhesive is applied to either surface of the green-sheet. Preferably, the adhesive is a room-temperature adhesive. Such room-temperature adhesives have glass transition temperatures below room temperature, i.e., below about 20° C., so that they can bind substrates together at room temperature. Moreover, rather than undergoing a chemical change or chemically reacting with or dissolving components of the substrates, such room-temperature adhesives bind substrates together by penetrating into the surfaces of the substrates. Sometimes such room-temperature adhesives are referred to as "pressure-sensitive adhesives." Suitable room-temperature adhesives are typically supplied as water-based emulsions and are available from Rohm and Haas, Inc. and from Air Products, Inc. For example, a material sold by Air Products, Inc. as "Flexcryl 1653" has been found to work well.

The room-temperature adhesive may be applied to the green-sheet by conventional coating techniques. To facilitate coating, it is often desirable to dilute the supplied pressure-sensitive adhesive in water, depending on the coating technique used and on the viscosity and solids loading of the starting material. After coating, the room-temperature adhesive is allowed to dry. The dried thickness of the film of room-temperature adhesive is preferably in the range of 1 to 10 microns, and the thickness should be uniform over the entire surface of the green-sheet. Film thicknesses that exceed 15 microns are undesirable. With such thick films of adhesive voiding or delamination can occur during firing, due to the large quantity of organic material that must be removed. Films that are less than about 0.5 microns thick when dried are too thin because they provide insufficient adhesion between the layers.

From among conventional coating techniques, spin-coating and spraying are the preferred methods. If spin-coating is used, it is preferable to add 1 gram of deionized water for every 10 grams of "Flexcryl 1653." If spraying is used, a higher dilution level is preferred to facilitate ease of spraying. Additionally, when room-temperature adhesive is sprayed on, it is preferable to hold the green-sheet at an elevated temperature, e.g., about 60 to 70° C., so that the material dries nearly instantaneously as it is deposited onto the green-sheet. The instantaneous drying results in a more uniform and homogeneous film of adhesive.

After the room-temperature adhesive has been applied to the green-sheet layers, the layers are stacked together to form a multilayered green-sheet structure. Preferably, the layers are stacked in an alignment die, so as to maintain the desired registration between the structures of each layer. When an alignment die is used, alignment holes must be added to each green-sheet layer.

Typically, the stacking process alone is sufficient to bind the green-sheet layers together when a room-temperature adhesive is used. In other words, little or no pressure is required to bind the layers together. However, in order to effect a more secure binding of the layers, the layers are preferably laminated together after they are stacked.

The lamination process involves the application of pressure to the stacked layers. For example, in the conventional lamination process, a uniaxial pressure of about 1000 to 1500 psi is applied to the stacked green-sheet layers that is then followed by an application of an isostatic pressure of about 3000 to 5000 psi for about 10 to 15 minutes at an elevated temperature, such as 70° C. Adhesives do not need to be applied to bind the green-sheet layers together when the conventional lamination process is used.

However, pressures less than 2500 psi are preferable in order to achieve good control over the dimensions of such structures as internal or external cavities and channels. Even lower pressures are more desirable to allow the formation of larger structures, such as cavities and channels. For example, if a lamination pressure of 2500 psi is used, the size of well-formed internal cavities and channels is typically limited to no larger than roughly 20 microns. Accordingly, pressures less than 1000 psi are more preferred, as such pressures generally enable structures having sizes greater than about 100 microns to be formed with some measure of dimensional control. Pressures of less than 300 psi are even more preferred, as such pressures typically allow structures with sizes greater than 250 microns to be formed with some degree of dimensional control. Pressures less than 100 psi, which are referred to herein as "near-zero pressures," are most preferred, because at such pressure few limits exist on the size of internal and external cavities and channels that can be formed in the multilayered structure.

The pressure is preferably applied in the lamination process by means of a uniaxial press. Alternatively, pressures less than about 100 psi may be applied by hand.

As with semiconductor device fabrication, many devices may be present on each sheet. Accordingly, after lamination the multilayered structure may be diced using conventional green-sheet dicing or sawing apparatus to separate the individual devices. The high level of peel and shear resistance provided by the room-temperature adhesive results in the occurrence of very little edge delamination during the dicing process. If some layers become separated around the edges after dicing, the layers may be easily re-laminated by applying pressure to the affected edges by hand, without adversely affecting the rest of the device.

The final processing step is firing to convert the laminated multilayered green-sheet structure from its "green" state to form the finished, substantially monolithic, multilayered structure. The firing process occurs in two important stages as the temperature is raised. The first important stage is the binder burnout stage that occurs in the temperature range of about 250 to 500° C., during which the other organic materials, such as the binder in the green-sheet layers and the organic components in any applied thick-film pastes, are removed from the structure.

In the next important stage, the sintering stage, which occurs at a higher temperature, the inorganic particles sinter together so that the multilayered structure is densified and becomes substantially monolithic. The sintering temperature used depends on the nature of the inorganic particles present in the green-sheet. For many types of ceramics, appropriate sintering temperatures range from about 950 to about 1600° C., depending on the material. For example, for green-sheet containing aluminum oxide, sintering temperatures between 1400 and 1600° C. are typical. Other ceramic materials, such as silicon nitride, aluminum nitride, and silicon carbide, require higher sintering temperatures, namely 1700 to 2200° C. For green-sheet with glass-ceramic particles, a sintering temperature in the range of 750 to 950° C. is typical. Glass particles generally require sintering temperatures in the range of only about 350 to 700° C. Finally, metal particles may require sintering temperatures anywhere from 550 to 1700° C., depending on the metal.

Typically, the devices are fired for a period of about 4 hours to about 12 hours or more, depending on the material used. Generally, the firing should be of a sufficient duration so as to remove the organic materials from the structure and to completely sinter the inorganic particles. In particular, polymers are present as a binder in the green-sheet and in the room-temperature adhesive. The firing should be of sufficient temperature and duration to decompose these polymers and to allow for their removal from the multilayered structure.

Typically, the multilayered structure undergoes a reduction in volume during the firing process. During the binder burnout phase, a small volume reduction of about 0.5 to 1.5% is normally observed. At higher temperatures, during the sintering stage, a further volume reduction of about 14 to 17% is typically observed.

As noted above, preferably any dissimilar materials added to the green-sheet layers are co-fired with them. Such dissimilar materials could be added as thick-film pastes or as other green-sheet layers. The benefit of co-firing is that the added materials are sintered to the green-sheet layers and become integral to the substantially monolithic microfluidic device. However, to be co-fireable, the added materials should have sintering temperatures and volume changes due to firing that are matched with those of the green-sheet layers. Sintering temperatures are largely material-dependent, so that matching sintering temperatures simply requires proper selection of materials. For example, although silver is the preferred metal for providing electrically conductive pathways, if the green-sheet layers contain alumina particles, which require a sintering temperature in the range of 1400 to 1600° C., some other metal, such as platinum, must be used due to the relatively low melting point of silver, (961° C.).

The volume change due to firing, on the other hand, can be controlled. In particular, to match volume changes in two materials, such as green-sheet and thick-film paste, one should match: (1) the particle sizes; and (2) the percentage of organic components, such as binders, which are removed during the firing process. Additionally, volume changes need not be matched exactly, but any mismatch will typically result in internal stresses in the device. But symmetrical processing, placing the identical material or structure on opposite sides of the device can, to some extent, compensate for shrinkage mismatched materials.

Too great a mismatch in either sintering temperatures or volume changes may result in defects in or failure of some or all of the device. For example, the device may separate into its individual layers, or it may become warped or distorted.

Figure 2:
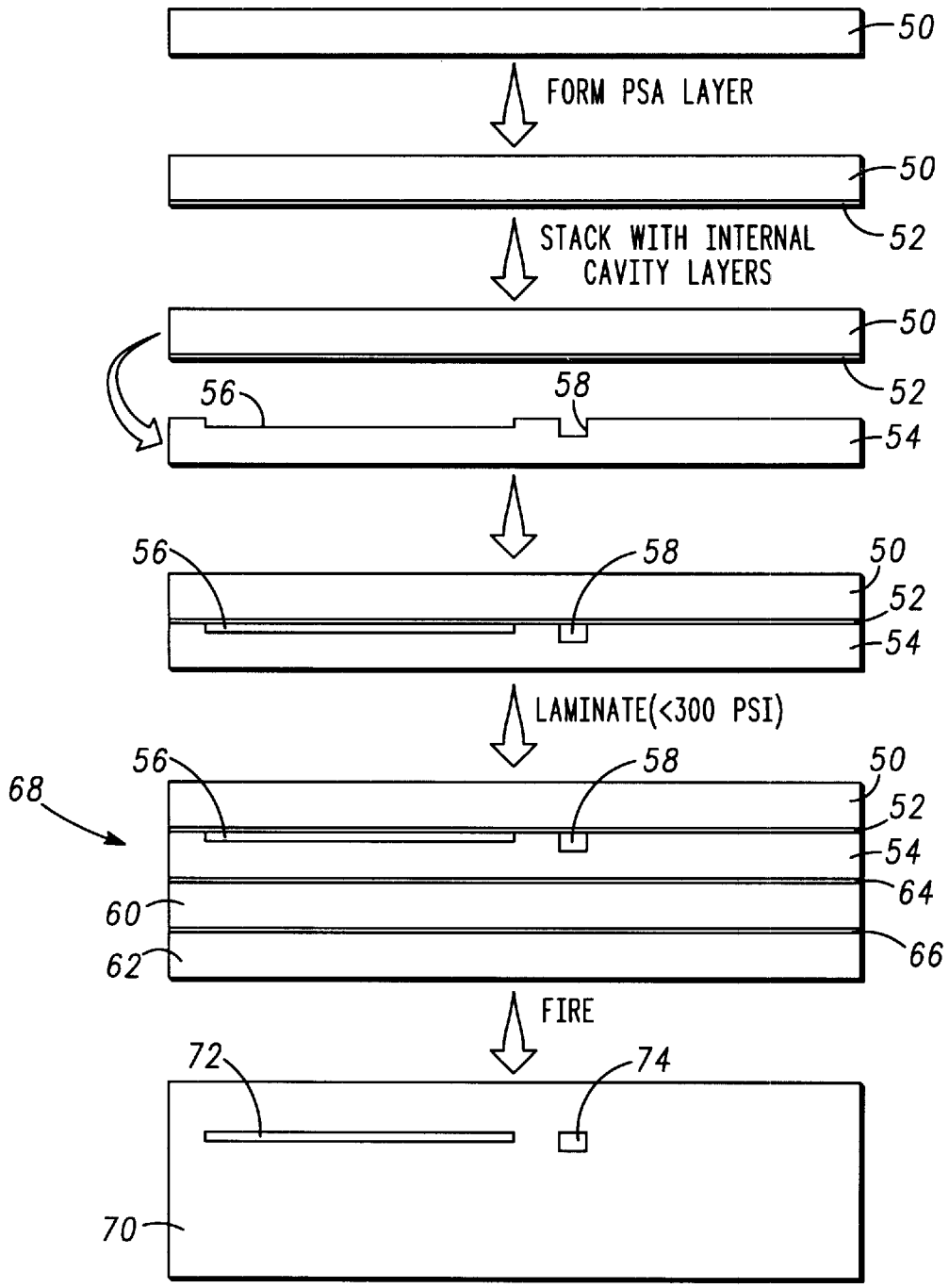
FIG. 2 is a schematic representation of the steps for making a multilayered microfluidic device, in accordance with an embodiment of the present invention.

FIG. 2 summarizes the aforementioned steps, schematically illustrating cross-sections of typical layers that would be used to form a multilayered microfluidic device in accordance with the present invention. A first green-sheet layer 50 is provided with a size appropriate for further processing. A room-temperature adhesive layer 52 is applied to one surface of green-sheet 50. First green-sheet layer 50 is then stacked with a second green-sheet layer 54, which has already been patterned with an internal channel 56 and an internal cavity 88. These layers are then stacked with two more green-sheet layers 60 and 62, with associated layers of room-temperature adhesive 64 and 66, to form the complete multilayered green-sheet structure 68. Multilayered green-sheet structure 68 is then laminated, as described above, and fired to form the final substantially monolithic structure 70.

The use of near-zero pressures, i.e., pressures less than 100 psi, for lamination is preferred because it allows the integrity of internal structures to be maintained, enabling internal channel 56 and internal cavity 58 formed in green-sheet layer 54 remain as an internal channel 72 and an internal cavity 74, respectively, in the final substantially monolithic structure 70. However, other lamination processes, including conventional high-pressure lamination process, could also be used, albeit with less control over the dimensions of internal structures.

The size of the final substantially monolithic structure 70 is shown smaller in FIG. 2 than the size of multilayered green-sheet structure 68 to reflect the volume reduction that occurs during firing.

Useful multilayered microfluidic devices would normally include, in addition to a fluid passageway, components that enable interaction with the fluid. Such components fall into three broad classes: (1) components that facilitate physical, chemical, or biological changes to the fluid; (2) components that allow the sensing of various characteristics of the fluid; and (3) components that control the motion of the fluid.

Each of these component classes will be discussed in turn, including how they may be realized in a multilayered microfluidic device formed from green-sheet layers. With each type of component, it is preferable that it be fabricated as part of the aforementioned processing steps in order to facilitate efficient and cost-effective mass-production. It is also preferred that such components be co-fired with and sintered to the green-sheet layers so as to form a part of the substantially monolithic structure of the finished device.

Components that cause physical or chemical changes to the fluid include components that change the temperature of the fluid and components that catalyze chemical reactions in the fluid. The simplest component for changing the temperature of the fluid is a heater.

Figure 3:
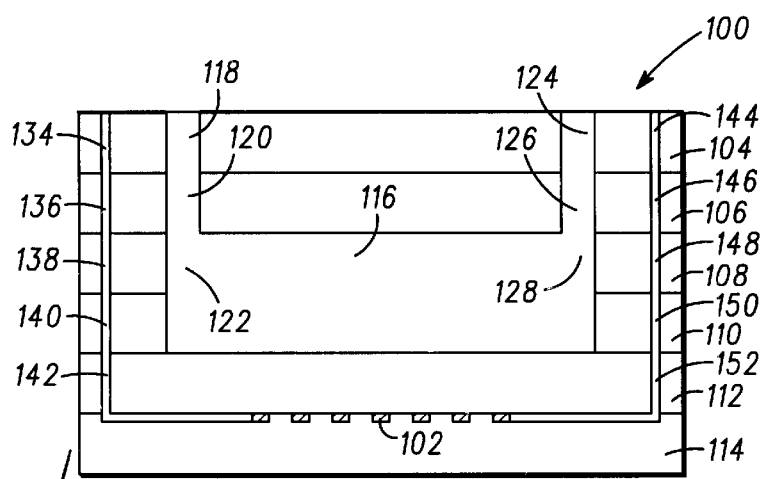
FIG. 3 is a schematic representation of part of a multi-layered microfluidic device having a horizontal heater, in accordance with an embodiment of the present invention.
Figure 3A:
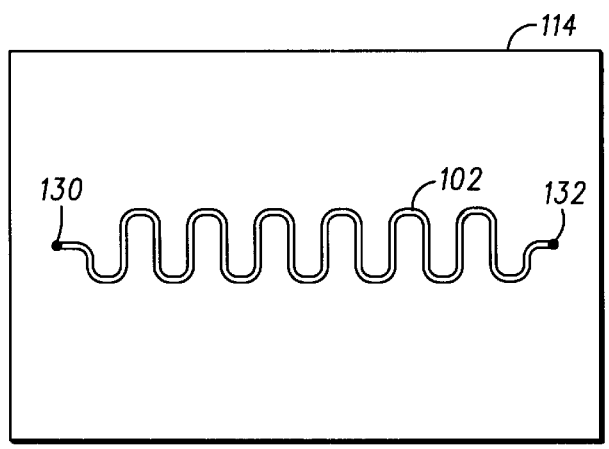
FIG. 3A is a partial view of the multilayered microfluidic device of FIG. 3, corresponding to a plan view of the bottom layer of the multilayered microfluidic device of FIG. 3.

Shown in FIG. 3 is a multilayered microfluidic device 100 in accordance with the present invention that includes a planar heater 102. Multilayered microfluidic device 100 is made up of layers 104–114. A cavity 116 is formed in layer 132. Cavity 116 is in fluid communication with the outside by means of vias 118, 120, and 122, which are formed in layers 104, 106, and 108, respectively. Cavity 116 is also in fluid communication with the outside by means of vias 124, 126, and 128, formed in layers 104, 106, and 108, respectively. As shown in cross-sectional view in FIG. 3, and in plan view in FIG. 3A, a heater 102 is formed by a serpentine trace of conductive material deposited on the surface of layer 114, and has terminals 130 and 132. Vias 134–142 are formed into layers 104–112, respectively, and are filled with a conductive material to provide an electrical conduction pathway between terminal 130 and the exterior of device 100. Similarly, vias 144–152 are formed into layers 104–112, respectively, and are filled with a conductive material to provide an electrical conduction pathway between terminal 132 and the exterior of device 100. External components (not shown) can make electrical contact with vias 134 and 144. In this configuration, an electrical current may be applied to heater 102 so that it maybe used to heat fluid in cavity 116. Although heater 102 is preferably separated from cavity 116 by layer 112, as shown in FIG. 3, heater 102 could also be placed on the upper surface of layer 112 so as to be in direct contact with the fluid in cavity 116.

Figure 4A:
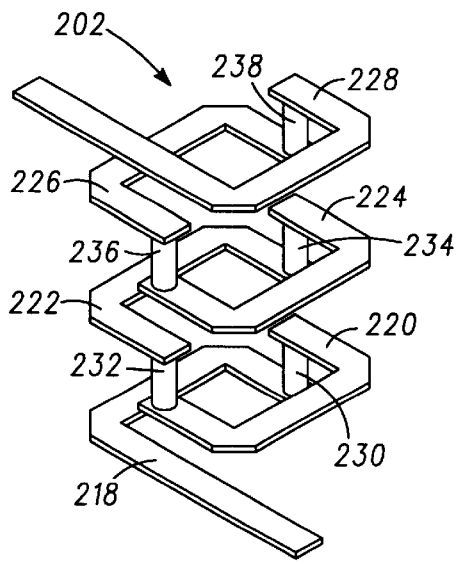
FIG. 4A is a perspective view of the vertical coil of FIG. 4.
Figure 4:
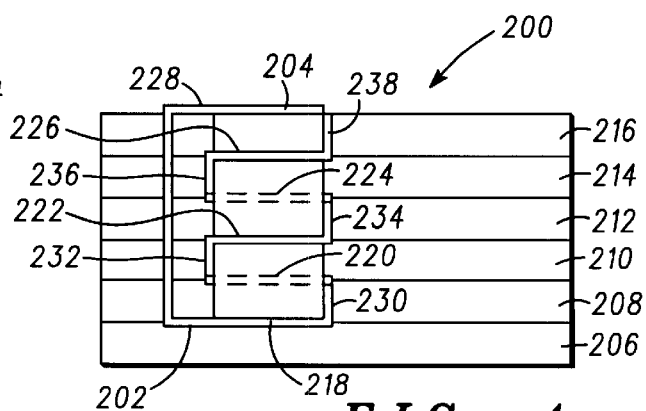
FIG. 4 is a schematic representation of part of a multi-layered microfluidic device, having a vertical coil wound around a cavity, in accordance with an embodiment of the present invention.

A heater incorporated into a multilayered microfluidic device may also be in the form of a coil, in either a vertical or horizontal orientation. Shown in FIG. 4 is part of a multilayered microfluidic device 200 that has a vertical coil 202 wound around a cavity 204. Device 200 is made up of layers 206–216. With reference to FIG. 4, and to FIG. 4A, which shows a perspective view of coil 202 in isolation, coil 202 comprises six horizontal windings 218–228, which are traces of conductive material deposited on layers 206–216, respectively, that are joined together by five conductor-filled vias 230–238 in layers 208–216, respectively.

Figure 5A:
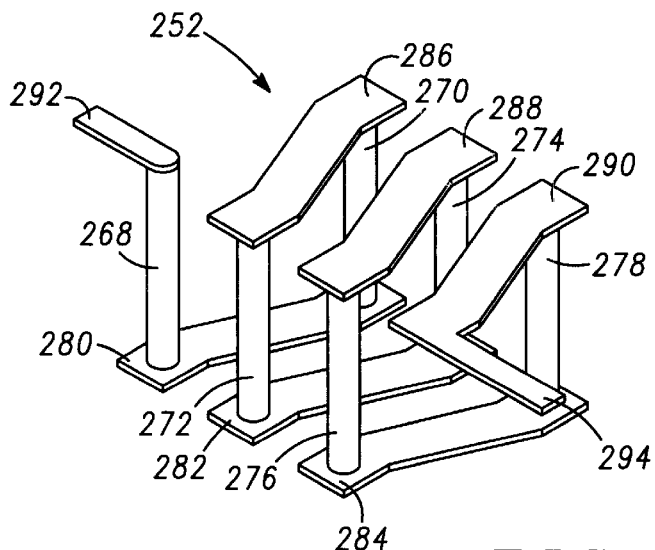
FIG. 5A is a perspective view of the horizontal coil of FIG. 5.
Figure 5:
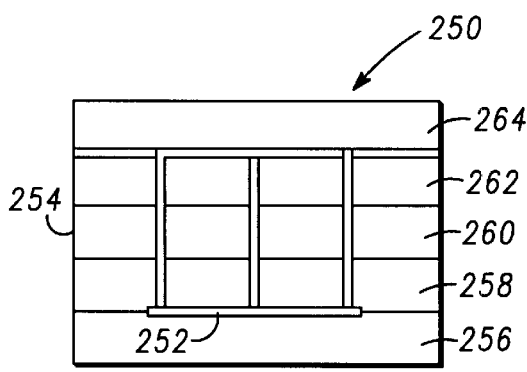
FIG. 5 is a schematic representation of part of a multi-layered microfluidic device, having a horizontal coil wound around a channel, in accordance with an embodiment of the present invention.

Shown in FIG. 5 is part of a multilayered microfluidic device 250 that has a a horizontal coil 252 wound around a channel 254. Device 250 is made up of layers 256–264. With reference to FIG. 5, and to FIG. 5A, which shows a perspective view of coil 252 in isolation, coil 252 includes six vertical elements 268–278, each of which comprises stacked conductor-filled vias formed in layers 258–262. Vertical elements 268–278 are interconnected by three lower horizontal elements 280–284 and three upper horizontal elements 286–290, arranged in an angular offset from lower elements 266–270. Lower elements 280–284 are traces of conductive material deposited on layer 256, and upper elements 286–290 are traces of conductive material deposited on layer 262. Electrical current is directed to coil 252 by means of a lead 292, connected to vertical element 268, and a lead 294, connected to horizontal element 290. Leads 292 and 294 are traces of conductive material deposited on layer 262.

Whether the heater is planar, as heater 102, in the form of a coil, as in coil 202 and 252, for the element to operate efficient as a heater, it should have a much higher resistance than that of the electrical conduction pathway that leads to it. The conductors that make up the heater are preferably about 5 mils to 8 mils to in diameter, while the conductors that lead to the heater are preferably about 20 to 30 mils wide.

Figure 6:
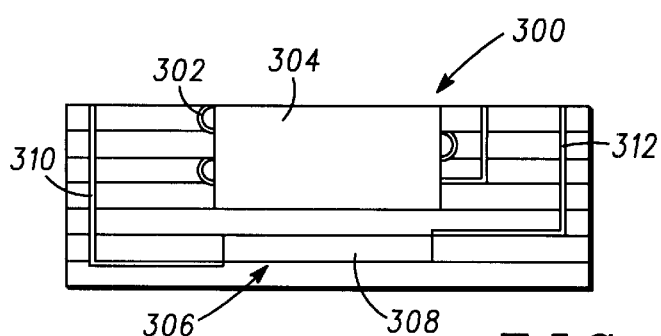
FIG. 6 is a schematic representation of part of a multi-layered microfluidic device, having a thermoelectric element, in accordance with an embodiment of the present invention.

More flexible control of fluid temperature is achieved by using additional components. For example, shown in FIG. 6 is a part of a multilayered microfluidic device 300 in accordance with the present invention that includes a vertical heater coil 302 wound about a cavity 304, as well as a thermoelectric cooling element 306. Thermoelectric cooling element 306 includes a thermoelectric element 308, sintered into one of the layers near cavity 304, and a pair of leads 310 and 312, made up of conductive traces deposited on the layers and conductor-filled vias.

The provision of both heater 302 and cooling element 306 allows for much better control over the temperature of the fluid in cavity 304. For example, the ability to both heat and cool the fluid in cavity 304 allows different processing steps requiring different temperatures to take place in cavity 304. In particular, thermoelectric cooling element 306 can be used to cool cavity 304 more rapidly after heater 302 is turned off. As another example, heater 302 and cooling element 306. can be used together, along with a temperature measurement device (not shown), so as to dynamically maintain the temperature of cavity 304 at a fixed level.

Figure 7:
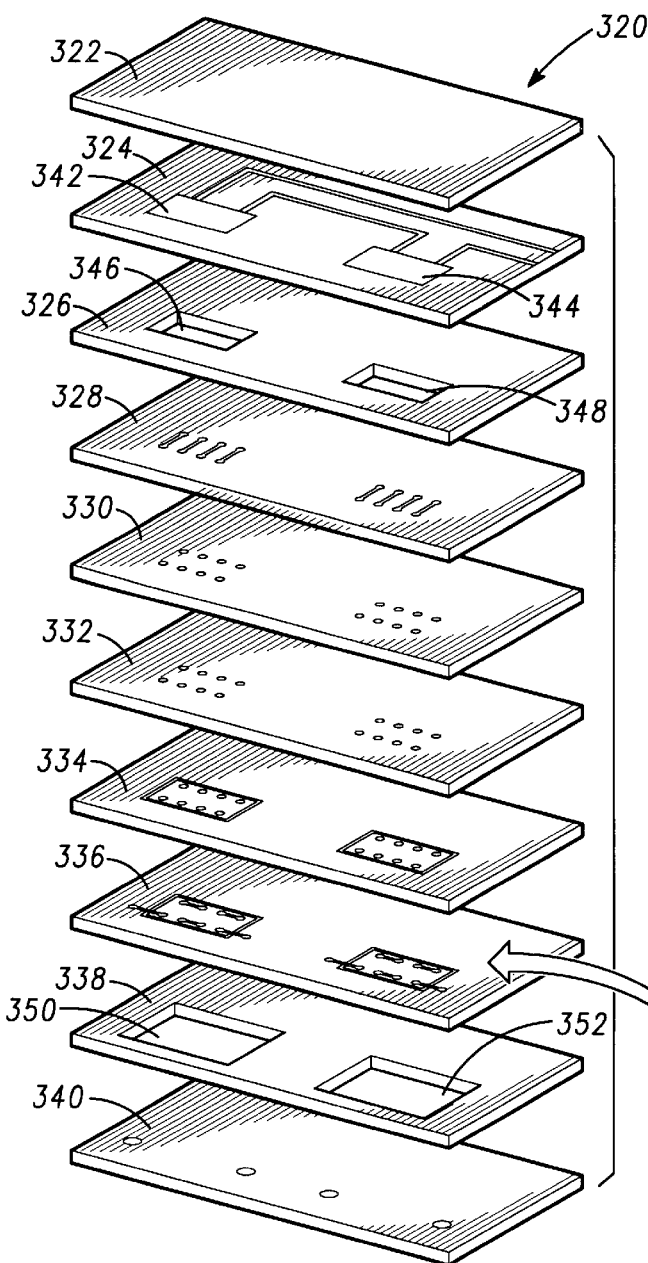
FIG. 7 is an exploded schematic representation of part of a multilayered microfluidic device, having two thermoelectric elements, in accordance with an embodiment of the present invention.

FIG. 7 shows the structure of a preferred thermoelectric element in more detail. A multilayered microfluidic device 320 is made up of green-sheet layers 322–340. A pair of cavities 342 and 344 are formed in layer 324. A pair of thermal dispersers 346 and 348 are made of silver screen-printed onto the upper surface of layer 326, so as to form the bottom surface of cavities 324 and 344. Similarly, a pair of thermal dispersers 350 and 352 are made of screen-printed silver on layer 338. A pair of thermoelectric elements 354 and 356 made up of a series of interconnected vias that are formed into layers 328–336 and filled with thermoelectric material. When current is applied to them, thermoelectric elements 354 and 356 transfer heat from thermal dispersers 350 and 352 to thermal dispersers 346 and 348, thereby cooling cavities 342 and 344.

The thermoelectric material is preferably $Si_{0.8}Ge_{0.2}$ that has been doped, either with phosphorus to be n-type or with boron to be p-type. This material may be co-fired with the green-sheet layers at 850° C. in a reducing atmosphere.

Figure 7A:
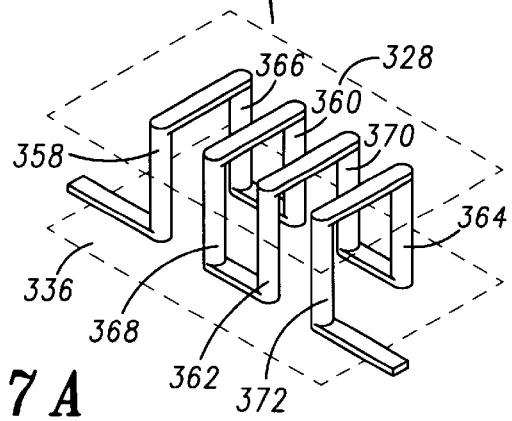
FIG. 7A is a schematic view of one of the thermoelectric elements of FIG. 7.

FIG. 7A shows how the vias are preferably interconnected in thermoelectric element 356. Four sets of stacked vias 358–364 are filled with n-type thermoelectric material, and another four sets of stacked vias 366–372 are filled with p-type thermoelectric material. The n-type vias 358–363 and p-type vias are interconnected in series by conductive traces screen-printed on layers 328 and 336, as shown in FIG. 7A.

Figure 8:
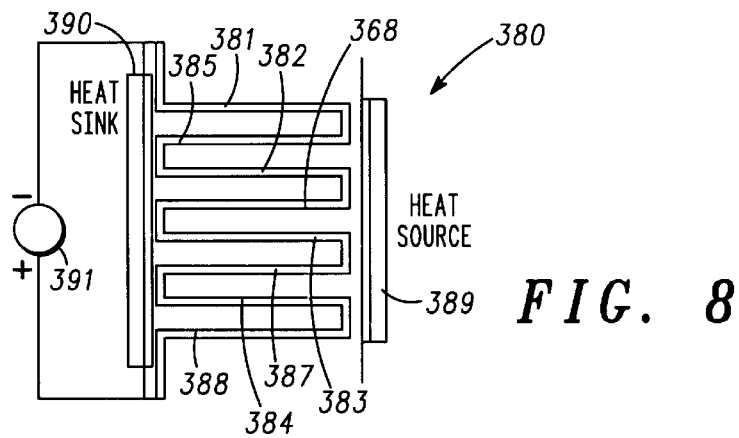
FIG. 8 is a schematic representation of an alternate configuration for a thermoelectric element, in accordance with an embodiment of the present invention.

A thermoelectric element 380 can also be fabricated in a planar configuration, as shown in FIG. 8. In this configuration, n-type thermoelectric material is screen-printed onto a green-sheet layer to define four n-type traces 381–384, and p-type thermoelectric material is screen-printed onto the green-sheet layer to define four traces 385–388. N-type traces 381–384 and p-type traces 385–388 extend from a heat source 389 to a heat sink 390. N-type traces 381–384 and p-type traces 385–388 are connected in series, as shown in FIG. 8, so that when a voltage from a voltage source 391 is applied, thermoelectric element 380 transfers heat from heat source 389 to heat sink 390.

Although thermoelectric elements are typically used for cooling, they can also be used for heating by reversing polarity. For example, thermoelectric element 308 and heater coil 302 can be used together to heat cavity 304. This will often result in more uniform heating.

Figure 9:
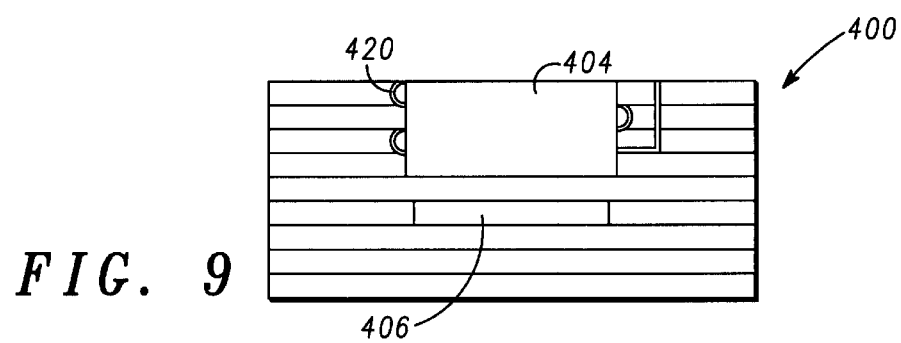
FIG. 9 is a schematic representation of part of a multi-layered microfluidic device, having a thermal isolation pocket, in accordance with the present invention.

FIG. 9, which shows part of a multilayered microfluidic device 400 in accordance with the present invention, illustrates the important concept of thermal isolation. In particular, different processes occurring simultaneously or near-simultaneously in different parts of the device may require different temperatures. Accordingly, it is often desirable to provide thermal isolation between different parts of the device so that different temperatures can be maintained. In device 400, a vertical heater coil 402 is wound around a cavity 404, and an internal cavity 406 is formed in a layer below cavity 404. Cavity 406, which preferably lacks any inlet or outlet, is kept empty to provide thermal isolation because of its low thermal conductivity compared to the rest of the device. In addition to empty cavities, thermal isolation can be provided by adding layers of low thermal conductivity or by adding low thermal conductivity materials to the green-sheet layers.

Figure 10:
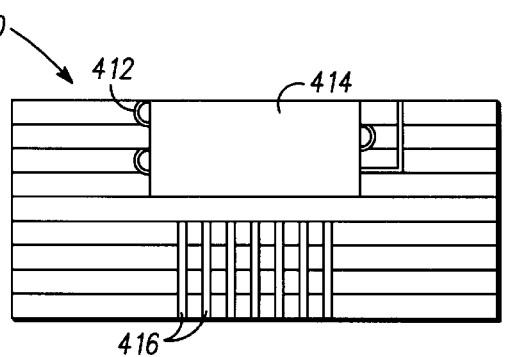
FIG. 10 is a schematic representation of part of a multi-layered microfluidic device, having a plurality of thermal vias, in accordance with the present invention.

FIG. 10, which shows a part of a multilayered microfluidic device 410 in accordance with the present invention, illustrates yet another approach to temperature control. Device 410 includes a vertical heater coil 412 would around a cavity 414 and a series of thermal vias 416 formed in the layers below cavity 414. Thermal vias 416 preferably comprise stacked vias that are filled with a high thermal conductivity material, such as the pastes used for providing conductive traces, that have been sintered to the green-sheet layers. Thermal vias 416 act as heat sinks, facilitating heat exchange with the fluid in cavity 414. Thermal vias 416 may extend to the outer surface of device 410 to be thermally coupled with external heating or cooling elements, such as electrical heaters, thermoelectric cooling elements, cooling fins, or heat exchangers. Thermal vias 416 may also provide a thermal pathway to internal components, such as electrical heaters and thermoelectric cooling elements.

Figure 11:
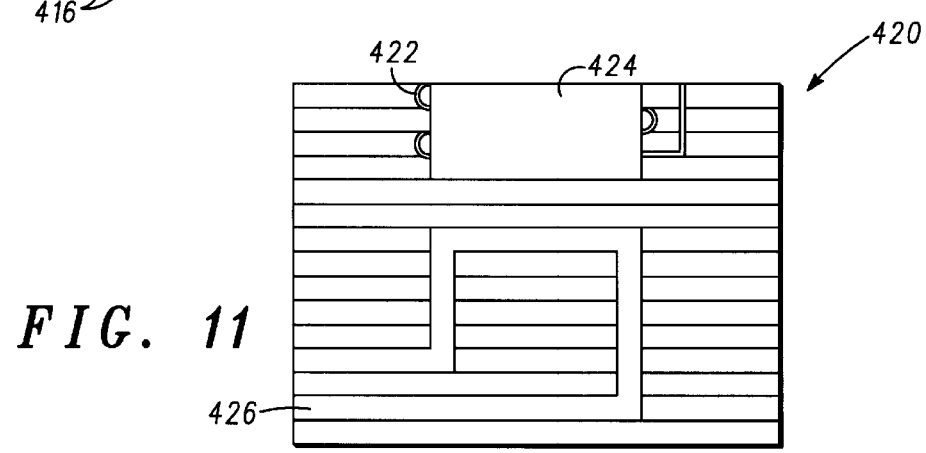
FIG. 11 is a schematic representation of part of a multilayered microfluidic device, having a heat exchanger, in accordance with the present invention.

Shown in FIG. 11 is a part of a multilayered microfluidic device 420, in accordance with the present invention. Device 420 includes a vertical heater coil 422 wrapped around a cavity 424 and a heat exchanger 426. Heat exchanger 426 comprises a fluid passageway, such as a series of channels and vias, in which a fluid flow is directed. At least a portion of heat exchanger 426 is adjacent to cavity 424 for good thermal contact. Thermal vias (not shown in FIG. 11) may be added between heat exchanger 426 and cavity 424 for improved heat exchange. In this way, the flow of fluid through heat exchanger 426 can serve to either add or remove heat from the fluid in cavity 424, thereby raising or lowering the temperature of the fluid.

Causing chemical changes in the fluid is also important in many multilayered microfluidic devices. In many cases, a plurality of fluid passageways in the device will direct a plurality of fluids together for chemical reaction. Alternatively, fluids may be added sequentially to a cavity serving as a reaction chamber.

Many chemical reactions can also be facilitated by heterogeneous catalysts. Such heterogeneous catalysts are most commonly metals, such as platinum, palladium, and rhodium. Catalysts may be added to multilayered microfluidic devices by means of thick-filled technology. In this approach, a thick-film paste containing particles of the metal (the inorganic phase) dispersed in a binder is applied to a surface of a green-sheet, before lamination, at a location that corresponds to a cavity or channel in the finished device. During the firing step, the fugitive materials are expelled from the thick film, leaving behind a thick metal film that is also sintered to the material of the green-sheet.

Figure 12:
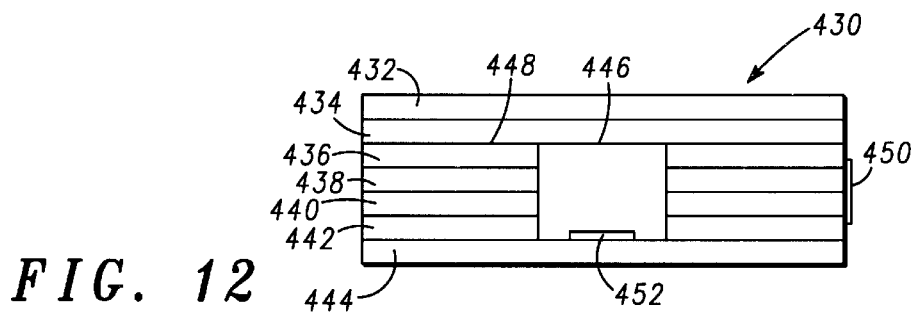
FIG. 12 is a schematic representation of part of a multilayered microfluidic device, having a heterogeneous catalyst in a reaction chamber, in accordance with an embodiment of the present invention.

Shown in FIG. 12 is a part of a multilayered microfluidic device 430, in accordance with the present invention. Device 430 includes layers 432–444. A cavity 446 is formed in layers 436–442. Cavity 446 is connected to a first channel 448, formed in layer 436, and a second channel 450, formed in layer 438. A thick-film heterogeneous catalyst 452 is sintered to layer 444 within cavity 446. In device 430, cavity 446 serves as a reaction chamber. A reactant or reactants flows into cavity 446 from one or both of channels 448 and 450. The desired chemical reaction is induced by catalyst 452, and the reaction product flows out of cavity 446 through one or both of channels 448 and 450.

Some reactions may be facilitated by electrochemical catalysis. For such applications device 430 may be fabricated with an electrical lead (not shown) extending to catalyst 452 so as to apply a voltage to catalyst 452. The electrical lead (not shown) may comprise a series of screen-printed conductor traces and conductor-filled vias (not shown) in layers 432–444.

Preferably, catalyst 452 is highly porous, so as to provide a high surface area for chemical reactions. Advantageously, the porosity of catalyst 452 can be controlled by adjusting the composition of the applied thick-film paste. In a typical thick-film paste, the inorganic phase is about 70–90 percent by weight, and this results in a dense thick-film after sintering. However, a more porous thick-film can be achieved by reducing the inorganic phase to about 40–60 percent by weight.

Additional control over the porosity of catalyst, 452 can be achieved by adding sub-micron polymer microspheres (preferably polystyrene or acrylic) to the thick-film paste. The material of the polymer microspheres should not be soluble in the binder and is preferably either polystyrene or acrylic. When the thick-film paste is deposited, the polymer microspheres are dispersed through the thick-film to define the pores that will ultimately be present in the sintered thick-film. During the sintering process, the polymer microspheres decompose, leaving behind controlled sub-micron pores within the sintered thick-film.

Causing biological changes in the fluid is also important in certain multilayered microfluidic devices of the present invention. One of the most important of these is the process of cell lysing. In this process, the walls of the cells present in the subject fluid are ruptured to release the cell contents, most notably the DNA. The released DNA may then be amplified, by means such as PCR or LCR, to provide a large enough sample for analysis. Cell lysing may be accomplished in the multilayered microfluidic devices of the present invention by chemical means, thermal means, by the application of strong electric fields, or by the application of microwave energy. In the present invention, cell lysing is preferably accomplished by the application of either strong electric fields or microwave energy. The microwave approach is most preferred.

Chemical cell lysing may be accomplished in a multilayered microfluidic device by holding the fluid containing the cells in a cavity, such as cavity 24 in device 10, shown in FIG. 1. The chemicals needed for cell lysis may then be introduced into cavity 24 through channel 26. Chemicals used for cell lysing include enzymes that digest the cell walls and detergents, such as sodium dodecyl sulfate, sodium lauryl sulfate, sarcosine, and Triton X-100.

Figure 19:
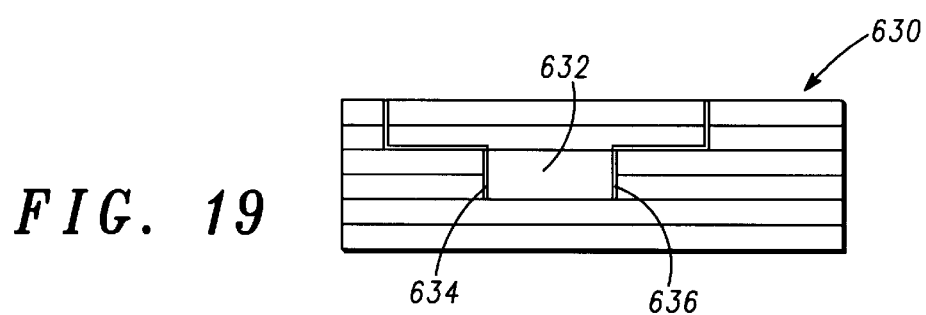
FIG. 19 is a schematic representation of part of a multilayered microfluidic device, having a resistive sensor, in accordance with an embodiment of the present invention.

Thermal cell lysing simply requires heating the fluid containing the fluid containing the cells to a sufficient temperature for a sufficient amount of time. For example, heating the cells at a temperature of 94° C. for two minutes is typical. Device 700, shown in FIG. 19, is suitable to accomplish thermal cell lysing in the multilayered microfluidic devices of the present invention. Fluid containing the cells is contained in cavity 720, and heater 722 applies the heat needed to maintain the temperature for the desired amount of time, as measured by thermal sensor 724.

Applying strong electric fields to the fluid containing the cells may also be used for cell lysis. Preferably, the electric field is a DC field in the range of about 1 kV/cm to 10 kV/cm. Further information about using electric fields for cell lysis is found in S. W. Lee, et al., "A Micro Cell Lysis Device," *Proceedings of IEEE: MEMS '98*, pp. 443–447 (1998), which is incorporated herein by reference.

To use this approach in the present invention, the fluid containing the cells is contained in a cavity to which the electric field is applied, preferably by means of parallel plates on opposite sides of the cavity. An example is device 570 shown in FIG. 16. The fluid containing the cells may be placed in cavity 572, and the electric field may be applied by plates 574 and 576.

Figure 13:
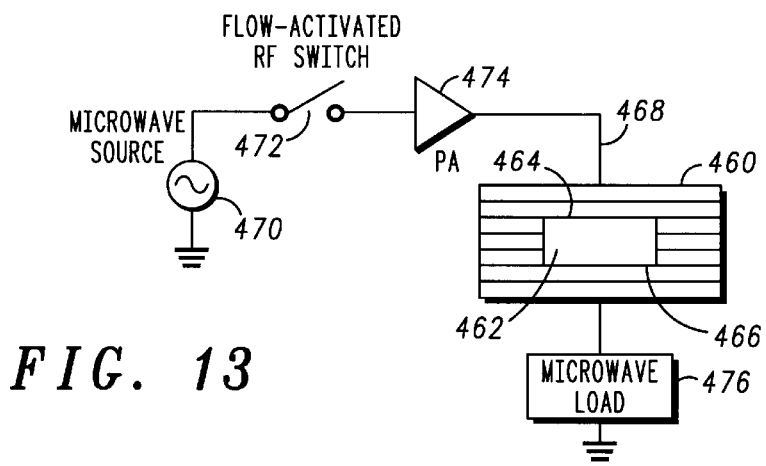
FIG. 13 is a schematic representation of part of a multilayered microfluidic device, having means for applying microwave energy for cell lysis, in accordance with an embodiment of the present invention.

The most preferred approach is to accomplish cell lysing by applying microwave energy. Shown in FIG. 13 is a part of a multilayered microfluidic device 460 that can be used for microwave cell lysing. Device 460 includes a cavity 462 in which the fluid containing the cells is placed. A pair of spaced-apart parallel plate electrodes .464 and 466 is provided on opposite walls of cavity 462. Electrodes 464 and 466 are preferably formed by sintering a metal-containing thick-film paste to the green-sheet layers. Electrodes 464 and 466 are part of an electrical circuit 468 that delivers microwave energy to cavity 462. Electrical circuit includes a microwave source 470, such as a magnetron or an RF source with harmonic output, a flow-activated RF switch 472, an RF power amplifier 474, and a microwave load 476, such as a resistor. Circuit 468 may be made up of external components, but, more preferably, the components of circuit 468 are made integral to device 460.

Fluid sensors are another class of important components in multilayered microfluidic devices. Fluid sensors allow the observation of various characteristics of the fluid, including without limitation its level, flow rate, temperature, pH, and optical characteristics.

Figure 14:
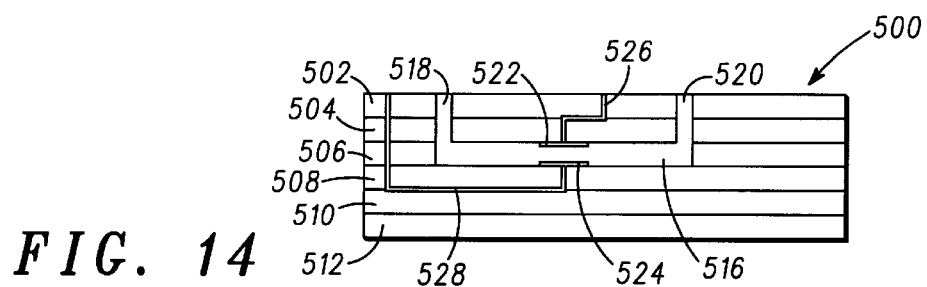
FIG. 14 is a schematic representation of part of a multilayered microfluidic device, having a capacitive sensor, in accordance with an embodiment of the present invention.

One such fluid sensor is a capacitive sensor. Shown in FIG. 14 is a part of a multilayered microfluidic device 500, in accordance with the present invention. Device 500 is made up of layers 502 and 512 and includes a channel 516, formed in layer 506, through which fluid is intended to flow. Channel 516 is connected to a fluid inlet 518 and a fluid outlet 520. Inlet 518 and outlet 520 are each defined by stacked vias formed in layers 502 and 504. A pair of spaced-apart parallel capacitor plates 522 and 524 are disposed on the walls of channel 516. Plates 522 and 524 are preferably formed by screen printing a metal-containing paste on the corresponding surfaces of green-sheet layers 504 and 508, respectively. Plates 522 and 524 are then co-fired with green-sheet layers 502–512, after these layers have been stacked and laminated together, to sinter the metal in plates 522 and 524 to the material in green-sheet layers 504 and 508, respectively. In this way, plates 522 and 524 become an integral part of device 500. Conductive leads 526 and 528 provide an electrically conductive pathway from plates 522 and 524, respectively, to the upper surface of layer 502, i.e., to the exterior of device 500, to allow for electrical connection to external components. Conductive leads are defined. by a series of conductive traces on the surfaces of and conductor-filled vias in layers 502–510.

Capacitor plates 522 and 524 define a capacitive sensor that is able to detect the presence or absence of fluid in channel 516 by sensing a change in capacitance. In particular, the dielectric constant of air is unity, whereas the dielectric constant of many fluids is much higher. For example, aqueous solutions have a dielectric constant in the region of 87. Accordingly, the introduction of fluid in channel 516 can be detected by an increase in capacitance between capacitor plates 522 and 524. Similarly, when all of the fluid is gone from channel 516, the capacitance will have decreased to its starting point. External components (not shown) electrically connected to leads 526 and 528 can be used to measure this capacitance. The external components (not shown) can also integrate the capacitance measurements over time so as to determine, in conjunction with the flow rate, the total amount of fluid that has flowed through channel 516.

In the embodiment shown in FIG. 14, the metal plates 522 and 524 of the capacitive sensor would be in direct contact with the fluid in the channel. However, this direct contact is often undesirable because certain fluids may react chemically with the metal. Additionally, the metal may not be compatible with many fluids containing biological materials.

Figure 15:
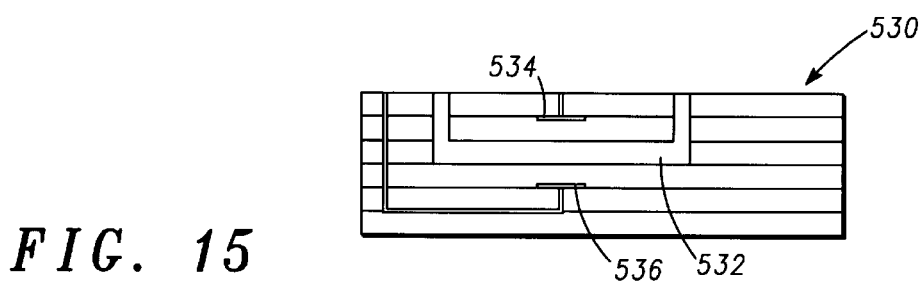
FIG. 15 is a schematic representation of part of a multilayered microfluidic device, having a capacitive sensor, in accordance with an embodiment of the present invention.

To obviate chemical reactivity and biocompatibility limitations, the metal plates of the capacitive sensor may be spaced away from the channel by one or more layers. This approach is shown in FIG. 15. Multilayered microfluidic device 530 is similar to device 500, except that capacitor plates 534 and 536 are each spaced away from channel 532 by one layer.

Figure 16:
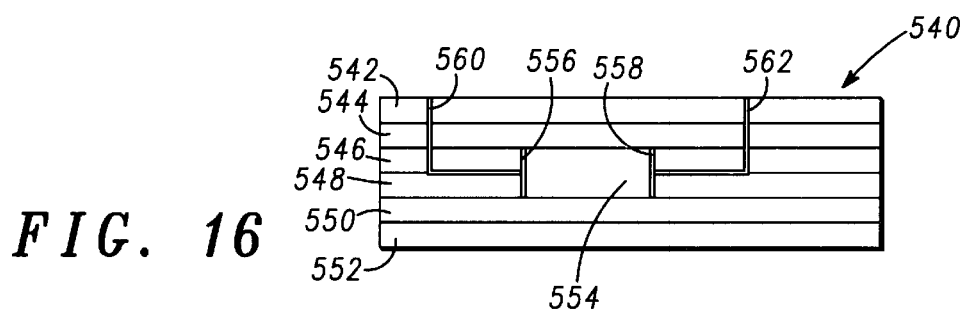
FIG. 16 is a schematic representation of part of a multilayered microfluidic device, having a capacitive sensor, in accordance with an embodiment of the present invention.

Capacitive sensors can also be used to measure fluid levels, such as in cavities that serve as wells of fluid. Shown in FIG. 16, is a part of a multilayered microfluidic device 540 that is made up of layers 542–552. A well 554 is formed in layers 546 and 548. Capacitor plates 556 and 558 are adjacent the opposite sides of the walls of well 554. Plates 556 and 558 may form part of the walls well 554, or they may be spaced away from the walls of well 554 so as not to be in direct contact with the fluid in well 554. Conductor leads 560 and 562 provide an electrical conduction path from plates 556 and 558, respectively, to the exterior of device 540, for connection to external components (not shown). Preferably, capacitor plates 556 and 558 each comprise conductor filled vias in layers 546 and 548 that are stacked together in registration. Preferably, the portion of each of capacitor plates 556 and 558 in each of the layers 546 and 548 comprises a row of vias, connected together, running parallel to and substantially the length of the adjacent wall of well 554. In this way, capacitor plates 556 and 558 each has an area substantially the same as the area of the adjacent wall of well 554. As an alternative construction, an area larger than well 554 may be punched out from green-sheet layers 546 and 548 and then filled with conductive paste. This conductor-filled area may then be punched out to define well 554 with conductive material remaining on opposite sides to define capacitor plates 556 and 558.

Well 554 is intended to contain fluid at a certain level. The level of the fluid in well 554 can be sensed by measuring the capacitance between plates 556 and 558. The higher the measured capacitance, the higher the fluid level.

Figure 17:
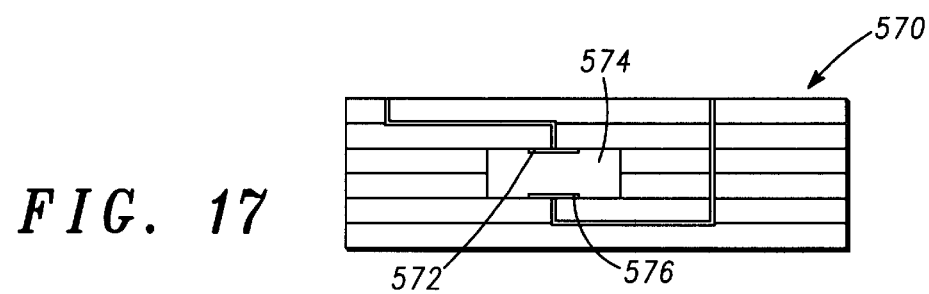
FIG. 17 is a schematic representation of part of a multilayered microfluidic device, having a capacitive sensor, in accordance with an embodiment of the present invention.

An alternate design is shown in FIG. 17. A multilayered microfluidic device 570 includes a well 572, and capacitor plates 574 and 576 located adjacent the top and bottom of well 572, respectively. Plates 574 and 576 may comprise part of the top and bottom walls of well 572, or they may be spaced away, such as by one or more layers, so as not to be in direct contact with the fluid in well 572.

Many fluids, such as ionic solutions, are conductive, so that their presence or absence in channels and wells can be detected by resistive sensors. Such resistive sensors comprise a pair of conductors that extend into a channel or cavity so that conductive fluid can complete an electrical circuit between them.

Figure 18:
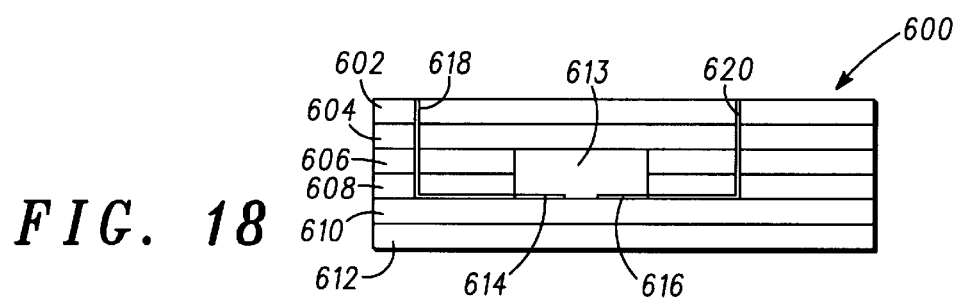
FIG. 18 is a schematic representation of part of a multilayered microfluidic device, having a resistive sensor, in accordance with an embodiment of the present invention.

Shown in FIG. 18 is part of a multilayered microfluidic device 600 that is made up of layers of 602–612. A well 613 is formed in layers 606 and 608. Deposited on the surface of layer 610 are conductors 614 and 616, each of which forms part of the bottom wall of well 613 so as to be in direct contact with any fluid in well 613. A series of stacked conductor-filled vias in layers 602–606 define leads 618 and 620, connected to conductors 614 and 616, respectively. Leads 618 and 620 extend to the exterior of device 600 so as to allow electrical connection to external components (not shown) for measuring the resistance between conductors 614 and 616. When no fluid is present in well 613, a very high resistance, i.e., an "open circuit" resistance, will exist between conductors 614 and 616. However, when conductive fluid is present in the well, current is able to flow between conductors 614 and 616 to provide a resistance that is lower than this "open circuit" resistance. In this way, conductors 614 and 616 comprise a resistive sensor able to sense the presence or absence of conductive fluid in well 613.

Alternate configurations are also available for the resistive sensor. Shown in FIG. 19 is a multilayered microfluidic device 630, having a well 632, in which conductors 634 and 636 form part of the walls of opposite sides of well 632. Conductors 634 and 636 may be formed by any of the methods described with respect to the fabrication of capacitor plates 556 and 558 in multilayered microfluidic device 540, provided that conductors 634 and 636 are able to directly contact fluid in well 632.

Another possible resistive sensor construction is shown in FIG. 14. In particular, capacitor plates 522 and 524 can also be used as the two conductors of a resistive sensor to sense the presence of conductive fluid in channel 522.

The presence or absence of fluid can also be detected by an inductive sensor. An inductive sensor is preferably in the form of a coil wound around a channel or cavity. For example, vertical coil 202, wound around cavity 204, as shown in FIGS. 4 and 4A, and horizontal coil 252, wound around channel 254, as shown in FIG. 5 and 5A, can serve as inductive sensors. Inductive sensors sense fluid by sensing changes in inductance. Most fluids have a magnetic permeability that differs only very little from that of air. As a result, the presence of such fluids by themselves is difficult to detect using inductive sensors. However, high permeability materials may be added to the fluids to make them easier to detect. Such high permeability materials preferably take the form of magnetic microspheres. Such magnetic microspheres are typically not permanent magnets, but rather they are paramagnetic. The paramagnetic material is typically an iron oxide. Such magnetic microshperes typically have sizes in the range of 0.1 to 10 microns. The paramagnetic material in the microspheres is preferably coated with or well dispersed in a polymer to render the microspheres nonreactive and biocompatible. Examples of magnetic microspheres suitable for use in the multilayered microfluidic devices of the present invention include catalog codes MC03N and MC05N, sold by Bangs Laboratories, Inc. of Fishers, Ind.

The surfaces of magnetic microspheres can also be used to interact with components of the fluid. For example, magnetic microspheres can provide surfaces on which chemical reactions can take place. Additionally, the structure and composition of the surfaces of magnetic microspheres can be controlled so that specific chemical and biological substances will bind to them. For example, DNA molecules can be attached to magnetic microspheres. The size of magnetic microspheres used to provide chemical reaction surfaces or binding sites is typically in range of 0.2 to 3 microns. The structure and application of magnetic microspheres is further described in Bob Sinclair, "To Bead or Not to Bead: Applications of Magnetic Bead Technology," The Scientist, vol. 12, no. 13 (Jun. 22, 1998), which is incorporated herein by reference.

For inductive sensing, the magnetic microspheres are added to the fluid introduced into the multilayered microfluidic device to give the fluid a high magnetic permeability. In this way, the presence or absence of fluid can be detected as changes in inductance. For example, coil 202 can be used to sense the fluid level in cavity 204. Specifically, with no fluid, and, thus, no magnetic microspheres present in cavity 204, the inductance of coil 202 will be relatively low. However, as the fluid level of cavity 204 rises, the number of magnetic microspheres in cavity 204 also rises, thereby increasing the inductance of coil 202. Similarly, changes in the inductance of coil 252 can be used to sense the presence or absence of fluid flowing through channel 254.

Figure 20:
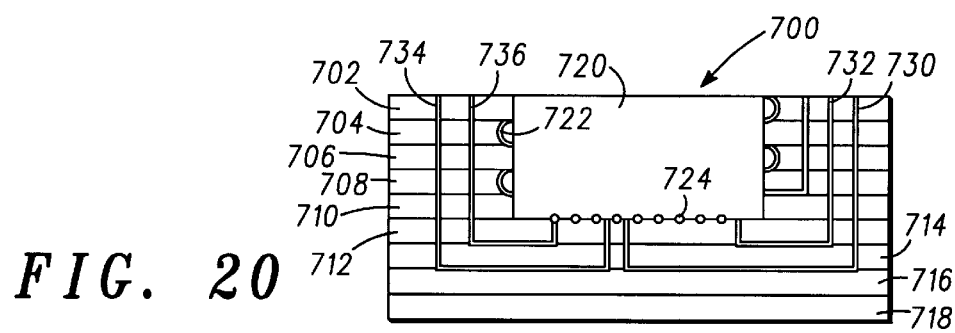
FIG. 20 is a schematic representation of part of a multilayered microfluidic device, having a temperature sensor, in accordance with an embodiment of the present invention.
Figure 20A:
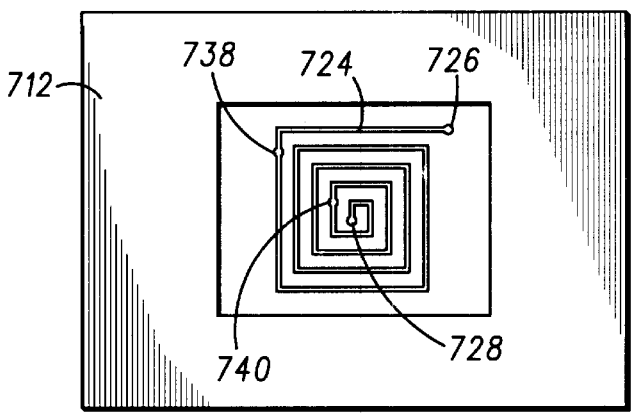
FIG. 20A is a partial view of the multilayered microfluidic device of FIG. 19, corresponding to a plan view of a layer of the multilayered microfluidic device of FIG. 19.

The multilayered microfluidic devices of the present invention may also include temperature sensors for measuring the temperature of the fluid. In many cases, the temperature sensor would be used in conjunction with a heater for control of the heating process. Shown in FIG. 20 is part of a multilayered microfluidic device 700, in accordance with the present invention. Device 700 is made up of layers 702–718. A cavity 720 is formed in layers 702–710, and a heater coil 722 is wound around cavity 720. One way of measuring the temperature of fluid in cavity 720 is by calculating the resistance of heater coil 722, based on the voltage and current applied to it. However, this method of fluid temperature measurement is likely to be inaccurate because of large differences between the temperature of heater coil 722 and the fluid.

A separate temperature sensor 724 provides a much more accurate measurement of the fluid temperature. As shown in FIGS. 19 and 19A, temperature sensor 724 is a trace of conductive material deposited on the upper surface of layer 712. Temperature sensor 724 preferably defines a spiral. Preferably, temperature sensor 724 is formed by screen printing a metal containing paste on green-sheet layer 712 that is then sintered to the material of layer 712 when device 700 is fired. The conductive material of temperature sensor 724 should have resistance that varies with temperature that is well-characterized. Terminals 726 and 728, which are also preferably screen printed on and sintered to layer 712, are provided at the ends of temperature sensor 724. Leads 730 and 732, which are defined by a series of conductor traces and conductor-filled vias in layers 702–716, electrically connect terminals to the exterior of device 700. In this way, external components (not shown) may be used to apply a current to temperature sensor 724 via leads 730 and 732. The temperature of the fluid in cavity 720 can then be determined from the resistance of temperature sensor 724.

Temperature sensor 724 can be made even more accurate by using it in a four lead configuration, as shown in FIG.

20A. Accordingly, it is preferable to provide two additional leads, leads 734 and 736, that are electrically connected to temperature sensor 724 at junctions 738 and 740. In this configuration, leads 730 and 732 apply a known current, while leads 734 and 736 measure the voltage drop between junction 738 and 740. The resistance, and, thus, the temperature, may then be calculated from the applied current and the measured voltage.

As shown in FIG. 20, layer 712 defines the bottom of cavity 720. Temperature sensor 712 would thus be in direct contact with any fluid in cavity 720. However, in applications where the material of temperature sensor 724 can react with, or is otherwise incompatible with, the fluid in cavity 720, temperature sensor 724 may also be spaced away from cavity 720 by one or more layers. For example, temperature sensor 724 could be located on the upper surface of layer 714 instead of layer 712.

Figure 21:
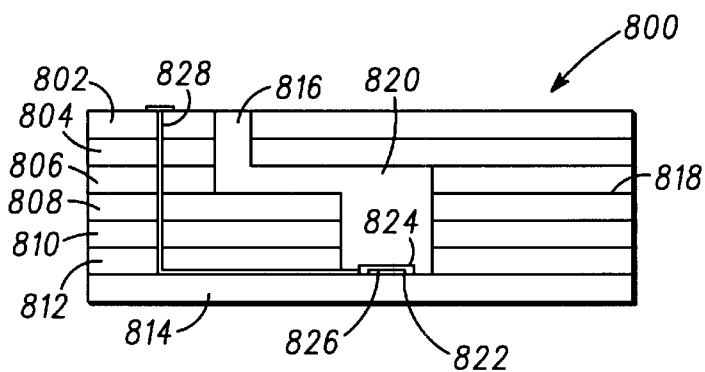
FIG. 21 is a schematic representation of part of a multilayered microfluidic device, having a pH sensor, in accordance with an embodiment of the present invention.

As many chemical and biochemical reactions depend on the pH environment, pH sensors can also be important components in the multilayered microfluidic devices of the present invention. Using thick-film technology, pH sensors can be sintered into channels and wells to sense the pH of the fluid there. Shown in FIG. 21 is part of such a multilayered microfluidic device that is made up of green-sheet layers 802–814. A first fluid passageway 816 is defined by layers 802–806, a second fluid passageway 818 is defined by layer 808, and a cavity is defined by layers 806–812. A thick-film pH sensor 822 is sintered to layer 814 and is located at the bottom of cavity 820. Thick-film pH sensor 822 comprises a layer of sensitive glass 824 on top of and sintered to a metal electrode 826. Both sensitive glass layer 824 and metal electrode 826 are preferably applied using thick-film technology. The thick-film paste used to form sensitive glass layer 824 may be made by mixing sensitive powders, preferably having particle sizes in the range of 10 to 20 microns, in an organic binder. The sensitive powders are typically mixtures of $Li_2O$, $CaO$, and/or $Na_2O$, with $SiO_2$. Using this composition, pH sensor 822 may be integrated with green-sheet layer 814 by sintering at a temperature of approximately 950° C. Further information regarding such thick-film pH sensors is found in J. H. Liu, et al., "Study of thick-film pH sensors," *Sensors and Actuators B,* 13–14 (1993), p. 566–567, which is incorporated herein by reference.

An electrical lead 828, preferably defined by a metal trace on layer 814 and metal-filled vias in layers 802–812, provides an electrically conductive pathway from electrode 826 to the outside of device 800. In this way, pH sensor 822 is sensitive to hydrogen ions present in the fluid contained in cavity 820 and, in combination with a reference electrode (not shown) external to device 800, pH sensor 822 may be used to measure the pH of the fluid in cavity 820.

Figure 22:
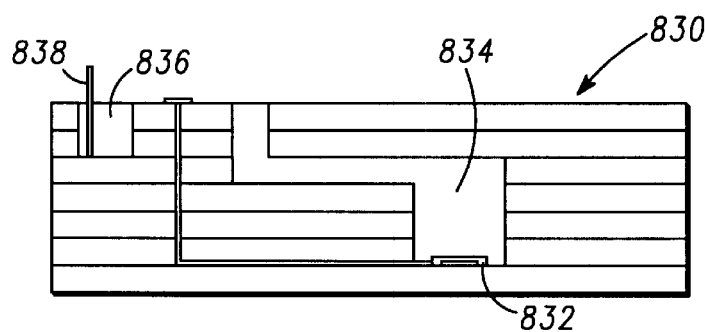
FIG. 22 is a schematic representation of part of a multilayered microfluidic device, having a pH sensor and a cavity for a reference solution, in accordance with an embodiment of the present invention.

Alternatively, the reference needed for pH measurement can be provided by the multilayered microfluidic device itself. As shown in FIG. 22, a multilayered microfluidic device 830, having a thick-film pH sensor 832 disposed in an internal cavity, 834 is provided with an external well 836 containing a reference solution. An external reference electrode 838 may be placed in the reference solution in external well 836 for pH measurement in combination with pH sensor 832.

Figure 23:
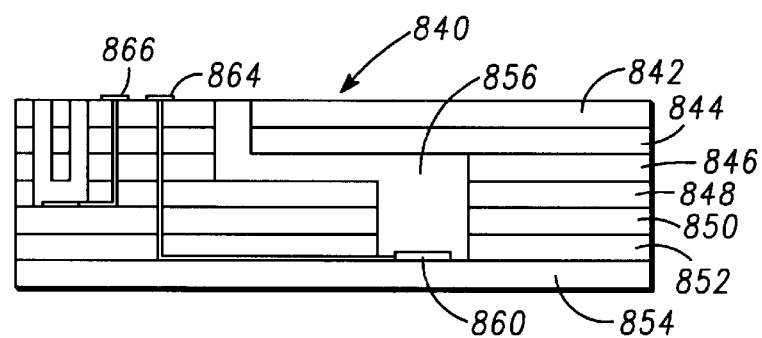
FIG. 23 is a schematic representation of part of a multilayered microfluidic device, having a pH sensor and an internal reference electrode, in accordance with an embodiment of the present invention.

Preferably, the reference electrode is integrated with the device. This approach is shown in FIG. 23. A multilayered microfluidic device 840, made up of green-sheet layers 842–854, includes a measurement cavity 856, defined by layers 846–852, and a reference cavity 858, defined by layers 846–848. A thick-film pH sensor 860 is sintered to layer 854 so as to be located at the bottom of measurement cavity 856, and a thick-film reference electrode 862 is sintered to layer 850, so as to be located at the bottom of reference cavity 858. Electrical leads 864 and 866, connect pH sensor 860 and reference electrode 862, respectively, to the outside of device 840 to allow electrical connection to external components (not shown). A reference solution may be added to reference cavity 858 to provide a reference for the pH measurement of fluid in cavity 856 by pH sensor 862. In this way, the number of external components (not shown) needed for pH is minimized.

Another important fluid sensing capability is the capability to sense the optical characteristics of the fluid in the channels and cavities of the device. In particular, the presence of certain chemical or biological substances in the fluid can be detected by observing the fluid's optical absorption at one or more wavelengths or by observing the extent to which the fluid emits light, such as through fluorescence, at one or more wavelengths. This approach can be used to monitor the progress of chemical reactions in the fluid. Such optical sensing requires materials, located between the channel or cavity containing the fluid, and the exterior of the device, that are optically transparent. As used herein, "optically transparent" and "optically transmissive" means being able to transmit visible and/or ultraviolet light.

Figure 24:
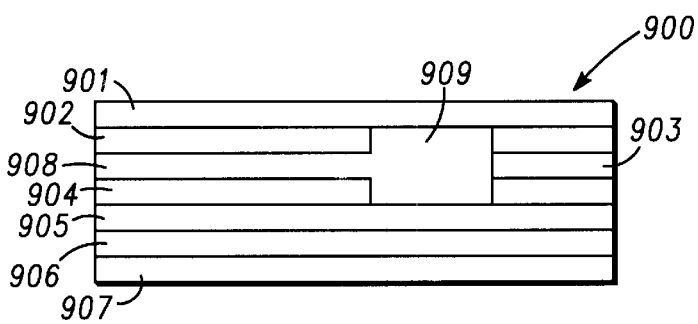
FIG. 24 is a schematic representation of part of a multilayered microfluidic device, having an optically transmissive layer, in accordance with an embodiment of the present invention.

One way of providing optical transparency is by providing a layer of an optically transmissive material on top of multiple opaque layers of green-sheet. For example, shown in FIG. 24 is part of a multilayered microfluidic device 900 made up of an optically transmissive layer 901 on top of opaque layers 902–907. A channel 908 is formed in layer 903, and a cavity 909 is formed in layers 902–904. Optically transmissive layer 901 can be made of glass, quartz, fused silica, a polymer, or any other material transparent in the desired range of wavelengths. Preferably, optically transmissive layer 901 is formed from a green-sheet, containing glass particles, that has been co-fired with layers 902–907 and, thereby, sintered to opaque layer 902. Alternatively, optically transmissive layer 901 can be attached after layers 902–907 are fired, such as by means of an adhesive. Preferably, the adhesive is a UV-polymerizable adhesive, such as Loctite 3492, sold by Loctite Corp., Hartford, Conn. However, other acrylic or urethane-based adhesives can be used. In the case where optically transmissive layer 901 is a polymer, it may also be attached by compression bonding or melt bonding.

As shown in FIG. 24, optically transmissive layer 901 provides optical access to cavity 909. Chemical reactions occurring in cavity 909 may be monitored optically, such as to determine when the reaction begins or when the reaction ends. Alternatively, fluid may be fed into cavity 909 from channel 908 merely for optical measurement.

The preferred optical sensing technique involves detecting the fluorescence of fluid in cavity 909. In this approach, source light at a first wavelength is applied to the fluid in cavity 909, through optically transmissive layer 901. The presence of fluorescent light, i.e., light at a second wavelength, emitted from the fluid in cavity 909 through layer 901 is then monitored. Fluorescent tagging molecules can be added to the fluid to facilitate this technique.

Alternatively, the intensity of the source light scattered from the fluid in cavity 909, through layer 901, may be measured so as to measure the absorptance or optical density of the fluid.

Figure 25:
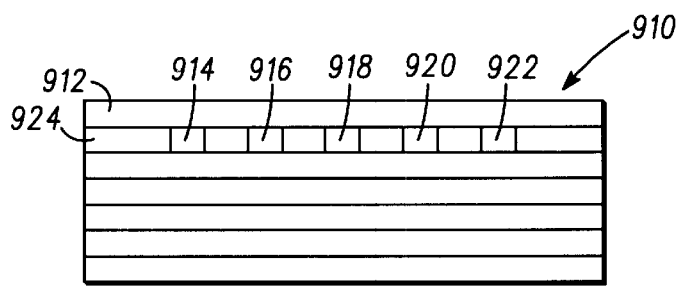
FIG. 25 is a schematic representation of part of a multilayered microfluidic device, having an optically transmissive layer, in accordance with an embodiment of the present invention.

Optical techniques can also be used to monitor different parts of the device simultaneously. Shown in FIG. 25, is part of a multilayered microfluidic device 910 that includes an optically transmissive layer 912 overlaying a plurality of cavities 914–922 formed into an opaque layer 924. Optically transmissive layer 912 provides optical access to each of cavities 914–922. Advantageously, chemical reactions may be run in parallel in cavities 914–922 and optically monitored simultaneously through optically transmissive layer 912.

Optical access can also be provided by filling vias with optically transmissive materials. In particular, vias may be filled with a thick-film paste that is optically transmissive after firing, such as thick-film pastes that contain glass particles. The filled vias are then fired with the rest of the device to provide optical vias, i.e., vias that do not allow the passage of fluid but are optically transmissive.

Alternatively, optical vias can be provided by filling the vias, such as by screen-printing, after the device is fired. The screen-printed materials in this approach preferably include acrylic or acrylic-urethane monomers that are then polymerized either thermally or by exposure to ultra-violet light to form optically transmissive polymers.

Figure 26:
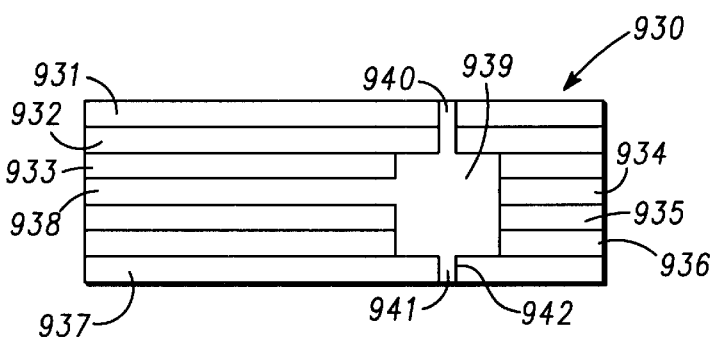
FIG. 26 is a schematic representation of part of a multilayered microfluidic device, having optical vias, in accordance with an embodiment of the present invention.

Shown in FIG. 26 is part of a multilayered microfluidic device 930 made up of opaque layers 931–937. A channel 938 is formed in layer 934, and a cavity 939 is formed in layers 933–936. Vias 940 and 941, which are filled with an optically transmissive material, are formed into layers 931 and 932, respectively, so as to be aligned together. In this way, stacked vias 940 and 941 provide optical access to fluid in cavity 939 from the top of device 930. A third via 942, filled with an optically transmissive material, may also be formed into layer 937 so as to provide optical access to fluid in cavity 939 from the bottom of device 930. Preferably, vias 940, 941, and 942 are all aligned together. In this way, light can pass directly through vias 940, 941, and 942, as well as any fluid in cavity 939, to allow for better measurement of the optical absorption of the fluid.

Figure 27:
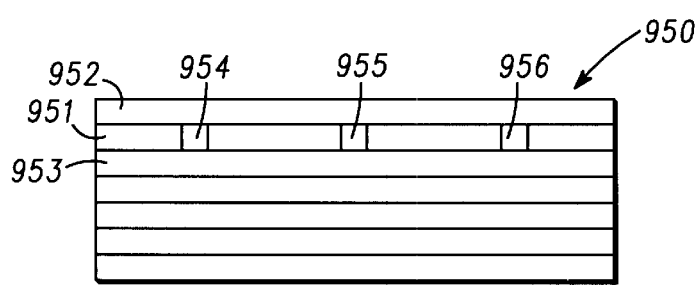
FIG. 27 is a schematic representation of part of a multilayered microfluidic device, having optical vias and an optically transmissive layer, in accordance with an embodiment of the present invention.

Filled vias can also be combined with optically transmissive layers, as shown in FIG. 27. In multilayered microfluidic device 950, an opaque layer 951 separates an optically transmissive layer 952 from a channel 952. Vias 954–956 are formed in layer 951 and are filled with an optically transmissive material. This arrangement allows the fluid to be optically sensed at different points in channel 953, such as to monitor the flow of the fluid through channel 953.

Horizontal optical access can also be provided in the multilayered microfluidic devices of the present invention. This may be accomplished by screen printing a thick-film paste that becomes optically transmissive after firing onto the surface of one of the green-sheet layers before the layers are laminated and fired. Alternatively optical fibers may be laminated between the green-sheet layers and then co-fired with the rest of the device.

Figure 28:
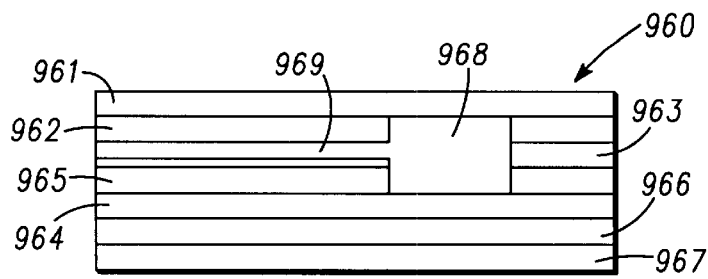
FIG. 28 is a schematic representation of part of a multilayered microfluidic device, having an optical fiber therein, in accordance with an embodiment of the present invention.

Shown in FIG. 28 is part of a multilayered microfluidic device 960 made up of opaque layers 961–967, in which a cavity 968 is formed in layers 962–964. An optical fiber 969, laminated between and sintered to layers 962 and 963, extends from the outer surface of device 960 to cavity. In this way, optical fiber 969 provides optical access to fluid in cavity 968. In the fabrication of device 960, it may be desirable to emboss channels into layers 962 and 963 before lamination in order to better accommodate optical fiber 969.

Figure 29:
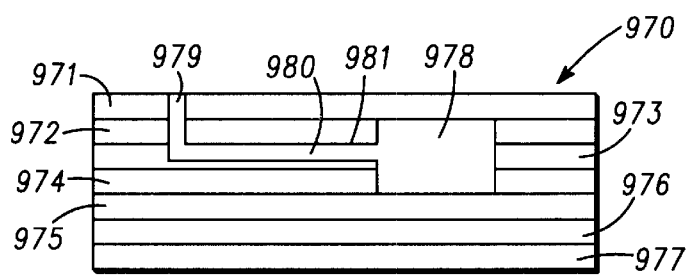
FIG. 29 is a schematic representation of part of a multilayered microfluidic device, having a horizontal and a vertical optically transmissive pathway, in accordance with an embodiment of the present invention.

Shown in FIG. 29 is part of a multilayered microfluidic device 970 made up of opaque layers 971–977, in which a cavity 978 is formed in layers 972–974. Stacked vias 979 and 980, formed into layers 971 and 972, respectively, are filled with an optically transmissive material sintered to layers, 971 and 972, such as may be provided by filling vias 979 and 980 with a thick-film paste containing glass particles. An optically transmissive trace 981 extends from filled via 980 to cavity 978. In this way, filled vias 979 and 980 and optically transmissive trace 981 provide optical access to fluid in cavity 978. Preferably, trace 981 is formed by depositing a thick-film paste, containing an optically transmissive material such as glass particles, onto the surface of green-sheet layer 973.

The third broad category of important components in the multilayered microfluidic devices of the present invention are components that control the motion of fluid or of components of the fluid. Included in this category are components that can serve as "pumps" by inducing fluid motion through channels.

Such pumping of fluids can be accomplished using electroosmotic pumping, which is suitable for conductive fluids, and electrohydrodynamic pumping, which is suitable for non-conductive fluids. Electroosmotic pumping of conductive fluid through a channel requires the application of an electric field, typically in the range of 100 to 500 volts percentimeter, across the length of the channel. Electroosmotic pumping is described in more detail in Andreas Manz, et al., "Electroosmotic Pumping and Electropheretic Separations for Miniaturized Chemical Analysis Systems," *Journal of Micromechanical Microengineering,* vol. 4, pp. 257–265 (1994), which is incorporated herein by reference.

Figure 30:
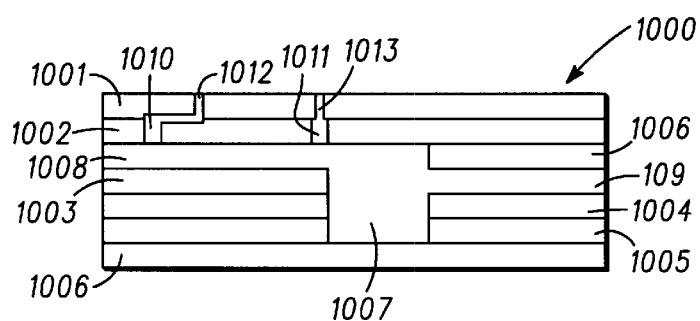
FIG. 30 is a schematic representation of part of a multilayered microfluidic device, having an electroosmotic pumping system, in accordance with an embodiment of the present invention.

Shown in FIG. 30, is part of a multilayered microfluidic device 1000, in accordance with the present invention, for performing electroosmotic pumping. Device 1000 is made up of layers 1001–1006. A cavity 1007 is formed in layers 1001–1006 A first channel 1008 is formed in layer 1006, and a second channel 1009 is formed in layer 1007. A pair of electrodes 1010 and 1011 are spaced along the length of channel 1008. Electrodes 1010 and 1011 are preferably defined by conductor-filled vias formed into layer 1002. Conductor leads 1012 and 1013 extend from electrodes 1010 and 1011, respectively, to the exterior of device 1000 for electrical connection to external components (not shown). In this way, the voltage required for electroosmotic pumping can be applied to electrodes 1010 and 1011. When this voltage is applied, fluid may be pumped through channel 1008 into cavity 1007.

Electrohydrodynamic pumping of relatively non-conductive fluids is preferably achieved by applying a traveling electric field along a fluid channel. For example, phase shifted voltage pulses may be applied sequentially to a series of electrodes spaced along the fluid channel. This approach is described in detail in G. Fuhr, "Pumping of Water Solutions in Microfabricated Eletrohydrodynamic Systems," *Micro Electro Mechanical Systems* '92 (Feb. 4–7, 1992), pp. 25–20, which is incorporated herein by reference.

Figure 31:
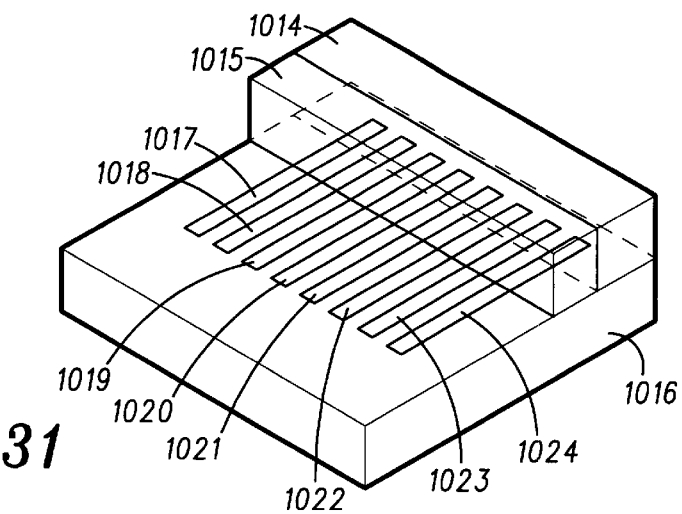
FIG. 31 is a schematic representation of part of a multilayered microfluidic device, having an electrohydrodynamic pumping system, in accordance with an embodiment of the present invention.

FIG. 31 shows schematically how electrohydrodynamic pumping may be achieved in the multilayered microfluidic devices in accordance with the present invention. Shown in FIG. 31 is a first green-sheet layer 1014 (shown as partially cut away), in which a channel 1015 is formed, and a second green-sheet layer 1015. A series of electrodes 1017–1024 are provided on the upper surface of green-sheet layer 1016 straddling channel 1015. Preferably, electrodes 1017–1024 are defined by conductive traces screen-printed and sintered into green-sheet layer 1016. Electrodes 1017–1024 are preferably evenly spaced, and the width of each of electrodes 1017–1024 are preferably substantially the same. To achieve electrohydrodynamic pumping, voltage pulses may be applied to each of electrodes 1017–1024 with a predetermined phase difference between each successive electrode. Thus, for example, the phase of the voltage pulses applied to electrodes 1017 and 1021 may be the same, with the phase of the voltage pulses varying continuously between the intermediate electrodes, 1018–1020. Preferably, the voltage pulses have a peak voltage in the range of 100 to 300 volts, and a frequency in the range of 100 kHz to 30 MHz. The spacing between electrodes is preferably about 200 microns. By applying voltage pulses in this way, fluid may be pumped through channel 1015.

The motion of piezoelectric members that are integrated into the multilayered microfluidic devices of the present invention can also be used to pump fluids. Such piezoelectric members are preferably made out of a ceramic material, preferably a lead zirconate titanate (PZT) material.

The PZT may be added to the green-sheet layers in one of several different ways. The PZT may be fired first and then added to a cavity provided in an unfired green-sheet layer. In this approach, the PZT may be secured in place by means of an adhesive, and electrodes may be provided for the piezoelectric member by applying a conductive epoxy.

Preferably, the PZT is co-fired with and sintered to the green-sheet layers so as to become an integral part of the device. For example, the PZT material can be cast as a ceramic green-sheet layer and then laminated and fired with the other green-sheet layers. Alternatively, the PZT material may be added to cavities in the unfired green-sheet layers as a thick-film paste. In either approach, electrodes may be provided on the piezoelectric members by screen printing metal-containing thick-film pastes onto them. In this way, the PZT material, electrodes, and green-sheet layers may all be co-fired. After firing, the PZT is poled by applying an electric field, typically greater than 2000 V/mm, by means of the electrodes deposited on it. The electrodes used for poling the PZT may be either the same as or different from the electrodes used for poling it.

PZT materials are a broad class of ceramic materials that can contain a wide variety of chemical components, but they all contain lead as a major component zirconate titanate of the form $Pb(Zr_{1-x}Ti_x)O_3$, where x can range from zero to one. Suitable sintering temperatures for this material are typically in the range of 1200° C. to 1300° C. However, a lower sintering temperature is required in order to co-fire this with many green-sheet materials. In particular, because the melting point of the preferred metallization material, silver, is only 961° C., the PZT materials used in the present invention preferably have a sintering temperature below this temperature. To lower the sintering temperature of PZT, various dopants may be added to it. For example, the sintering temperature of PZT may be lowered to 940° C. by the addition of 2.0 mol. % $Zn^{2+}$, added as ZnO, and 3.0 mol. % $Li^{1+}$, added as $Li_2CO_3$. Further details about this approach are provided by Z. Gui, et al., "Influence of Additives on Sintering Processing and Properties of High Performance Piezoelectric Ceramics," *Solid State Phenomena*, v. 25 & 26, pp. 309–316 (1992), which is incorporated herein by reference.

More preferably, the sintering temperature of PZT may be lowered even further, to about 900° C., as described in U.S. Pat. No. 5,792,379, which is incorporated herein by reference. In this approach, the PZT composition is characterized by 94.0 to 99.4 per cent by weight lead zirconate titanate, 0.1 to 1.0 percent by weight manganese dioxide, and 0.5 to 5.0 percent by weight glass additive having the formula $wB_2O_3$—$xBi_2O_3$—$yMeO$—$zCuO$, wherein Me is selected from the group consisting of Ca, Sr, Ba, and Zn. Additionally, w+x+y+z=1, where w ranges from 0.01 to 0.15, x ranges from zero to 0.80, y ranges from zero to 0.60, and z ranges from zero to 0.55.

Figure 32:
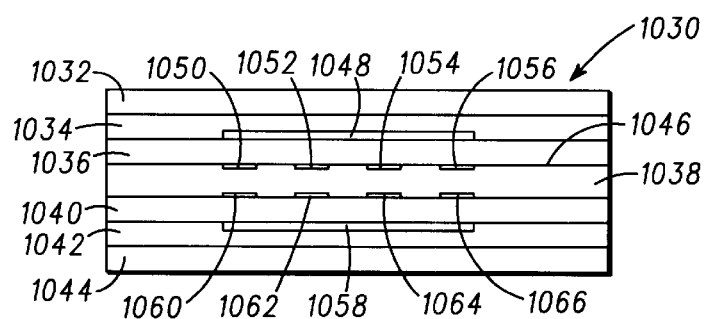
FIG. 32 is a schematic representation of part a multilayered microfluidic device, having a piezoelectric pumping system, in accordance with an embodiment of the present invention.

Shown in FIG. 32 is part of a multilayered microfluidic device 1030, in accordance with the present invention, that is provided with one type of piezoelectric pumping. Device 1030 is made up of layers 1032–1044, of which layers 1036 and 1038 are made out of a piezoelectric material and the other layers are formed from green-sheet containing non-piezoelectric materials. A channel 1046 is formed in layer 1038. An electrode 1048 is formed on the upper surface of piezoelectric layer 1036, and a series of electrodes 1050–1056 is formed on the lower surface of piezoelectric layer 1036. Similarly, an electrode 1062 is formed on the lower surface of piezoelectric layer 1040 and a series of electrodes 1060–1066 are formed on the upper surface of piezoelectric layer 1040. Electrically conductive leads (not shown), integral to device 1030, connect electrodes 1048–1066 to the exterior of device 1030, so that external components (not shown) can apply voltages to the electrodes. Preferably, the voltages applied to electrodes 1050–1056 and to 1060–1066 are timed so as to set up a surface acoustic wave. In particular, the parts of the piezoelectric layers 1034 and 1040 in contact with electrodes 1050–1056 and 1060–1066, respectively, alternately contract and relax in a coordinated fashion so as to draw fluid through channel 1038.

Figure 33:
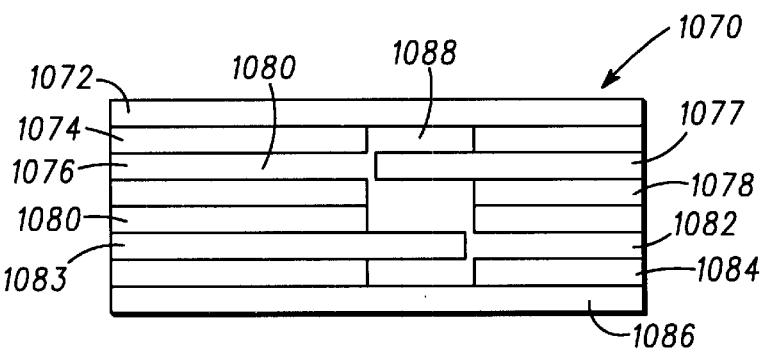
FIG. 33 is a schematic representation of part of a multilayered microfluidic device, having a piezoelectric pumping system, in accordance with an embodiment of the present invention.

Shown in FIG. 33 is a part of multilayered microfluidic device 1070, in accordance with the present invention, that is provided with another type of piezoelectric pumping. Device 1070 is made up of layers 1072–1086. Of these layers, layers 1076 and 1082 are, in part, made out of a piezoelectric material, thereby defining piezoelectric members 1077 and 1083. A cavity 1088 is formed in layers 1074–1084. Connected to cavity 1088 are an inlet channel 1090, formed in layer 1076, and an outlet channel 1092, formed in layer 1082. Piezoelectric members 1077 and 1083 can operate in two different ways to pump fluid from inlet channel 1076 into cavity 1088 and to pump fluid out of cavity 1088 through outlet channel 1092. In one mode of operation, members 1077 and 1083 alternately bend (either in the plane of the paper or perpendicularly to the plane of the paper) and relax in a coordinated fashion to draw fluid in from channel 1090 and to push fluid out into channel 1082. In another mode of operation, members 1077 and 1083 alternately elongate and contract in a coordinated fashion to move the fluid. Piezoelectric members 1077 and 1083 are provided with electrodes (not shown) in the appropriate locations to perform these operations.

Fluid pumps can also be based on the manipulation of magnetic beads. As noted above, magnetic microspheres can be added to the fluid in multilayered microfluidic devices, and certain chemical and biological substances can also be bound to the magnetic microspheres. Because the magnetic microspheres are paramagnetic, they preferably move to areas of magnetic flux density. Accordingly, electromagnets can be used to manipulate magnetic microspheres. The manipulation of magnetic microspheres, in turn, allows control over the placement and movement of the substances bound to them. As the magnetic microspheres move, they can also drag the surrounding fluid along them, thereby causing fluid flow.

Figure 34:
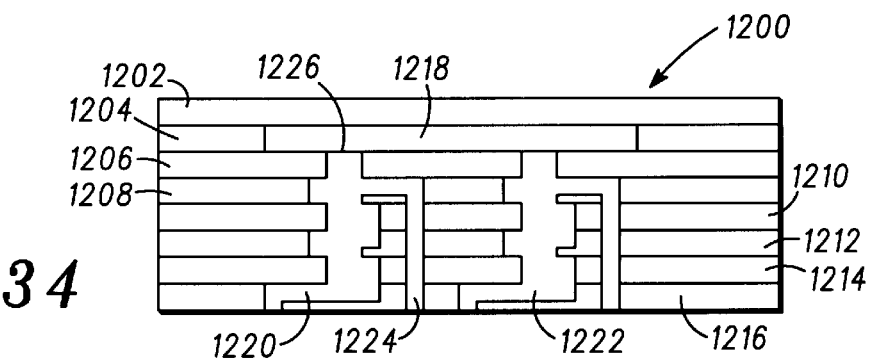
FIG. 34 is a schematic representation of part of a multilayered microfluidic device, having integrated electromagnets, in accordance with an embodiment of the present invention.

Shown in FIG. 34 is part of a multilayered microfluidic device 1200 in accordance with the present invention for electromagnetic manipulation of magnetic microspheres. Device 1200 is made up of green-sheet layers 1202–1216 and includes a channel 1218 formed in layer 1204. A pair of electromagnets 1220 and 1222 are aligned generally perpendicularly to channel 1218 so as to direct magnetic flux into channel 1218. Electromagnet 1220 is provided with a vertical coil 1224, defined by a series of conductive traces and conductor-filled vias in layers 1206–1216. Preferably, a core 1226 of high magnetic permeability material is placed within vertical coil 1224. The structure of electromagnet 1222 is similar to that of electromagnet 1220

Core 1226 is most conveniently defined by stacked vias in layers 1206–1214 that have been filled with the high permeability material. If the high permeability material of core 1226 is incompatible with the fluids that would flow through channel 1218, then core 1226 may be set back from channel 1218 by one or more layers. The high permeability material preferably includes a ferrite material, such as $Fe_3O_4$, $MnFe_2O_4$, or $CoFe_2O_4$. The ferrite may also be combined with glass frit. Suitable ferrite materials are SEI ferrite paste MPS #220, a thick-film paste containing ferrite materials, and SEI Green Tape, in which ferrite materials have been cast into a green-sheet, which are sold by Scrantom Engineering, Inc. of Costa Mesa, Calif. These commercially available materials may be sintered at a temperature in the range of 850–950° C. so as to integrate core 1226 with the rest of the device.

By applying current to electromagnet 1220 and/or electromagnet 1222, magnetic microspheres present in the fluid in channel 1218 may be moved around or held in place, as may be desired. For example, with electromagnet 1222 off and electromagnet 1220 on, the magnetic microspheres will be drawn towards electromagnet 1220 and may be held in place there. Electromagnet 1222 may then be turned on and electromagnet 1220 turned off, thereby causing the previously-held magnetic microspheres to move toward electromagnet 1222. In this way, magnetic microspheres may be moved along channel 1218. Accordingly, chemical or biological substances may be moved along channel 1218 in this way by binding them to the magnetic microspheres. The motion of magnetic microspheres can also drag fluid along them. In this way, electromagnets 1220 and 1222 maybe used to pump fluid through channel 1218. For fluid pumping, larger magnetic microspheres, i.e., those with sizes greater than about 5 microns, are preferred.

Although FIG. 34 shows only two electromagnets adjacent a channel, it is to be understood that a greater number of electromagnets may also be used to move microspheres through a channel. This motion is typically achieved by energizing the electromagnets sequentially, as described above. Electromagnets may also be used to move magnetic microspheres, and, thus, to pump fluid, into and out of cavities.

Figure 35:
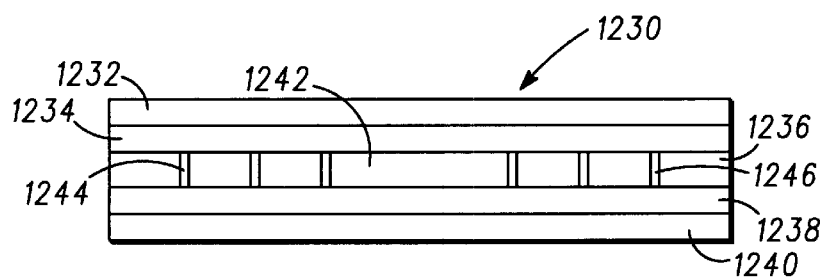
FIG. 35 is a schematic representation of part of a multilayered microfluidic device, having integrated electromagnets, in accordance with an embodiment of the present invention.

An alternate configuration is shown in FIG. 35, which shows part of a multilayered microfluidic device 1230 in accordance with the present invention. Device 1230 is made up of layers 1232–1240, with a channel 1242 formed in layer 1236. Wound about channel 1242 are first and second horizontal coils 1244 and 1246. Coil 1244 and 1246 are advantageously constructed out of a series of conductor traces and metal-filled vias in layers 1234–1240. Preferably, a material having a high magnetic permeability, such as a ferrite material, is incorporated into layers 1234 and 1238, which are adjacent to channel 1242. Coils 1244 and 1246 may be energized sequentially to move magnetic microspheres through channel 1242. For example, when coil 1244 is on and coil 1246 is off, magnetic microspheres will be drawn to coil 1244. Then, when coil 1244 is turned off and coil 1246 is turned on, the magnetic microspheres will move from coil 1244 to coil 1246.

Electromagnets can also be used for mixing or stirring fluids, which are very important processes in microfluidic devices. For example, the mixing of reactants is useful for promoting their chemical reaction. Stirring fluids also helps to achieve temperature uniformity and thermal equilibrium. When working with fluids containing magnetic microspheres, stirring is useful to promote dispersement of the microspheres through the fluid. However, because of the small dimensions of channels and wells in typical microfluidic devices, most fluid flow is laminar. Because mixing of fluids occurs primarily by diffusion in the laminar regime, efficient mixing is difficult to achieve unless a turbulent flow is developed.

Figure 36:
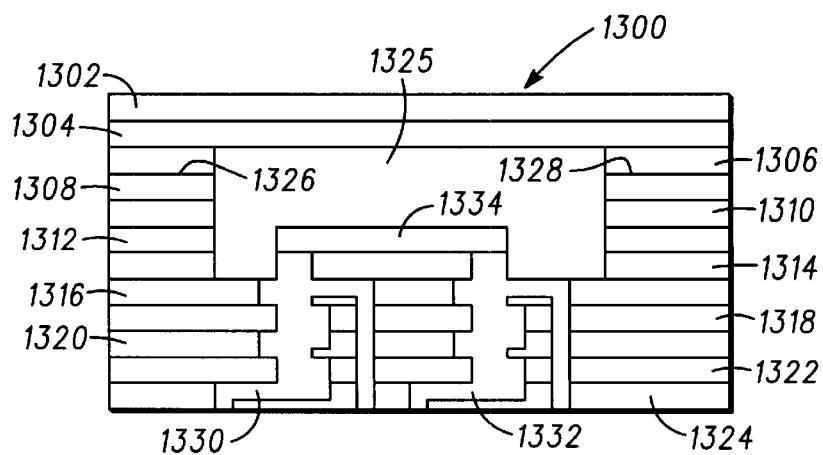
FIG. 36 is a cross-sectional schematic representation of part of a multilayered microfluidic device, having integrated electromagnets that control a magnetic stirring bar, in accordance with an embodiment of the present invention.
Figure 37:
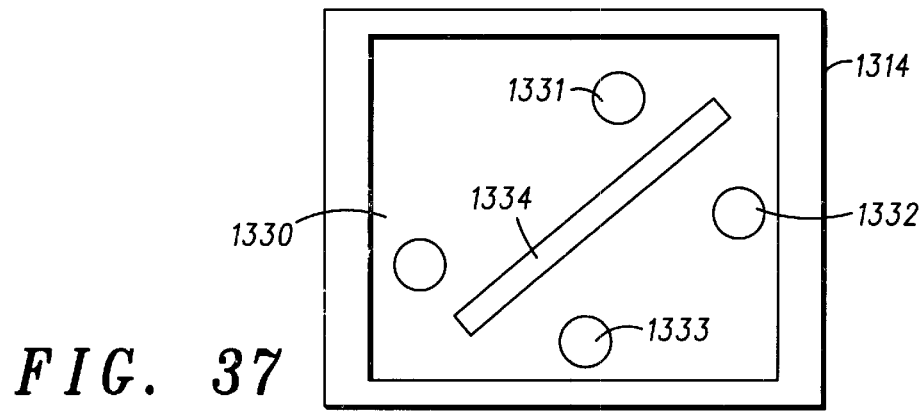
FIG. 37 is a top view schematic representation of part of a multilayered micro fluidic device, having integrated electromagnets that control a magnetic stirring bar, in accordance with an embodiment of the present invention.

Shown schematically in FIG. 36 is part of a multilayered microfluidic device made up of layers 1302–1322. A cavity 1325 is formed in layers 1306–1312. Channels 1326 and 1328, connected to cavity 1325, are formed in layer 1308. Electromagnets 1330 and 1332 are formed in layers 1314–1322. Preferably, electromagnets 1330 and 1332 each include a vertical coil, defined by a series of conductive traces and metal-filled vias, wound around a ferrite core that has been sintered into the green-sheet layers. A magnetic stirring bar 1334, which interacts with electromagnets 1330 and 1332, is disposed in cavity 1325. Although only two electromagnets are shown in FIG. 36, preferably at least four electromagnets are used to control stirring bar 1334. Shown schematically in FIG. 37 is a top view of layer 1314. Four electromagnets 1330–1333 are arranged symmetrically underneath cavity 1325.

In this configuration, magnetic stirring bar 1334 may be rotated by "rotating" the current supplied to electromagnets 1330–1333. For example, increasing the current to electromagnets 1330 and 1332, while decreasing the electric current to electromagnets 1331 and 1333, causes magnetic stirring bar 1334 to rotate so as to align itself with electromagnets 1330 and 1332. Then, decreasing the current to electromagnets 1330 and 1332, while increasing the electric current to electromagnets 1331 and 1333, causes magnetic stirring bar 1334 to rotate so as to align itself with electromagnets 1331 and 1333. Causing magnetic stirring bar 1334 to rotate in this way creates turbulent flow in the fluid in cavity 1325, thereby effecting good mixing.

Magnetic stirring bar 1334 may be added to cavity 1325, before layers 1302 and 1304 are applied, using conventional "pick-and-place" manufacturing equipment. Additionally, magnetic stirring bar 1334 should be larger than channels 1326 and 1328, so that after device 1300 has been fired, magnetic stirring bar 1334 will remain trapped within cavity 1325.

Another important class of components for controlling the motion of the fluid comprise components that act as valves. Because of the very small dimensions of typical channels in the multilayered microfluidic devices of the present invention, the interaction of the fluid with the walls of the channels becomes a very significant effect. Thus, valves may be conveniently provided as capillary stops in the fluid passageway. A capillary stop typically comprises a discontinuity or non-uniformity in the fluid passageway, which, because of the capillary action of the fluid, substantially blocks the flow of fluid at low pressures, but which allows the flow of fluid at higher pressures.

Figure 38:
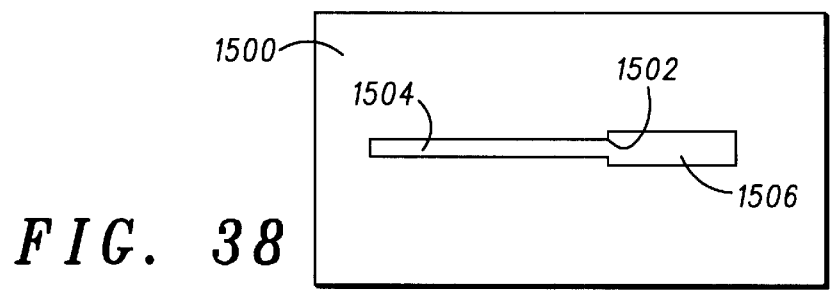
FIG. 38 is a top view schematic representation of a layer of a multilayered microfluidic device, having a capillary break, in accordance with an embodiment of the present invention.

One of the simplest structures that can act as a capillary stop is a discontinuity comprising an abrupt and substantial change in channel size. This type of discontinuity is often termed a capillary break. Shown in FIG. 38, is a layer 1500 in part of a multilayered microfluidic device, which layer includes a capillary break 1502. Specifically, capillary break 1502 is the discontinuity where a narrow channel 1504 joins a wide channel 1506. For example, narrow channel 1504 may be 5 mils wide, and wide channel 1506 may be 15 mils wide.

Capillary break 1502 functions in the following way. When fluid is introduced into wide channel 1506 at a low pressure, capillary action substantially prevents the fluid from flowing into narrow channel 1504. However, when the pressure applied to the fluid in wide channel 1506 exceeds a threshold value, the capillary action of the fluid at capillary stop 1502 becomes insufficient to hold the fluid back, with the result that fluid then flows into narrow channel 1504.

Capillary stops may also take the form of discontinuities in the surface energy of the walls of the fluid passageways. In particular, most of the glass, glass-ceramic, and ceramic materials commonly used in green-sheet layers are hydrophilic. However, hydrophobic materials may be applied to the surfaces of the fluid passageways to define hydrophobic regions within the fluid passageways. Such hydrophobic materials may include organo-silicon compounds and titanate and silane coupling agents. However, because such materials have a low decomposition temperature, they typically cannot be co-fired with the rest of the device.

The preferred hydrophobic materials are certain hydrophobic glass-ceramic materials, as these may be co-fired with and sintered to the green-sheet layers to provide hydrophobic regions within the fluid passageways. The preferred hydrophobic glass-ceramic materials contain the humite mineral norbergite ($Mg_2SiO_4 \cdot MgF_2$) as a major crystal phase and are described in U.S. Pat. No. 4,118,237, which is incorporated herein by reference. Thick-film pastes containing particles of these hydrophobic glass-ceramic materials may be added to fluid passageways by screen printing to define hydrophobic regions.

Figure 39:
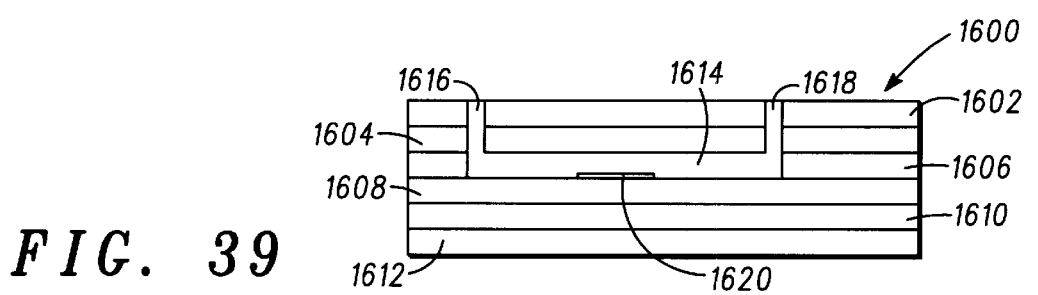
FIG. 39 is a schematic representation of part of a multilayered microfluidic device, having a hydrophobic region in a fluid passageway, in accordance with an embodiment of the present invention.

Shown in FIG. 39 is part of a multilayered microfluidic device 1600 made up of layers 1602–1612. A channel 1614 is formed in layer 1606, a fluid inlet 1616 comprises stacked vias formed into layers 1602 and 1604, and a fluid outlet 1618 also comprises stacked vias formed into layers 1602 and 1604. A hydrophobic region 1620 is disposed in channel 1614. Hydrophobic region 1620 is preferably formed by screen printing a thick-film paste containing a hydrophobic glass-ceramic material onto layer 1608 before lamination and then co-firing it, so that the hydrophobic material is sintered to layer 1608.

Hydrophobic region 1620 acts as a capillary stop. When fluid is applied to channel 1614 from fluid inlet 1616 at a low pressure, the fluid does not flow past hydrophobic region 1620 because of the discontinuity in surface energy. However, if the pressure applied to the fluid exceeds a threshold value, then the fluid is able to flow past hydrophobic region 1620 and out fluid outlet 1618.

Figure 40:
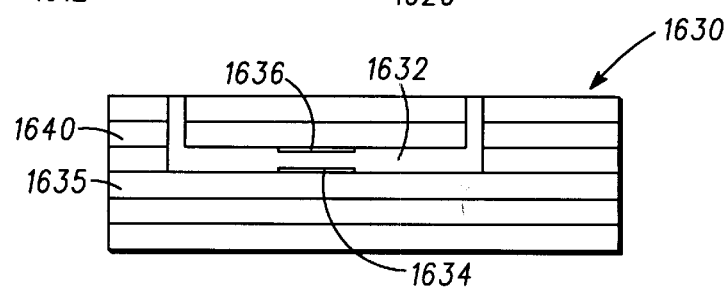
FIG. 40 is a schematic representation of part of a multilayered microfluidic device, having a pair of hydrophobic regions in a fluid passageway, in accordance with an embodiment of the present invention.

By using a pair of opposing hydrophobic regions in a channel, an even better capillary stop capability may be provided. For example, shown in FIG. 40 is part of a multilayered microfluidic device 1630 having a channel 1632, in which a pair of opposing hydrophobic regions 1634 and 1636 is disposed. Hydrophobic regions 1634 and 1636 are preferably formed by screen printing a hydrophobic glass-ceramic containing thick-film paste onto layers 1638 and 1640, which define the bottom and top walls of channel 1632, respectively.

Figure 41:
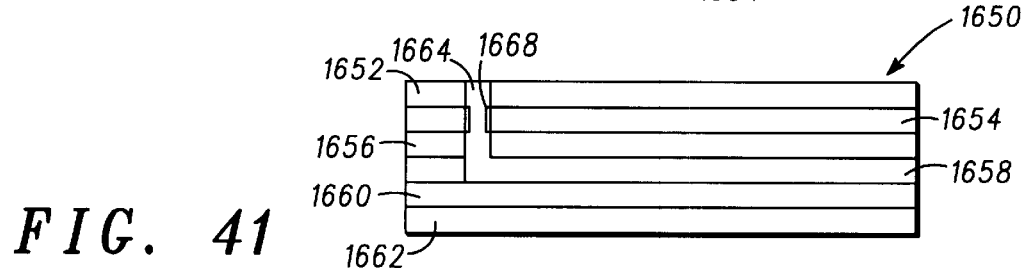
FIG. 41 is a schematic representation of part of a multilayered microfluidic device, having a hydrophobic region in a vertical fluid passageway, in accordance with an embodiment of the present invention.

Hydrophobic regions may also be provided in vertical channels. Shown in FIG. 41 is part of a multilayered microfluidic device 1650 formed from layers 1652–1662. A vertical channel 1664 is formed in layers 1652–1656, and a horizontal channel 1666 is formed in layer 1658. A hydrophobic region 1668, comprising a hydrophobic material sintered to layer 1654, encircles part of vertical channel 1664 to provide a capillary stop.

Figure 42:
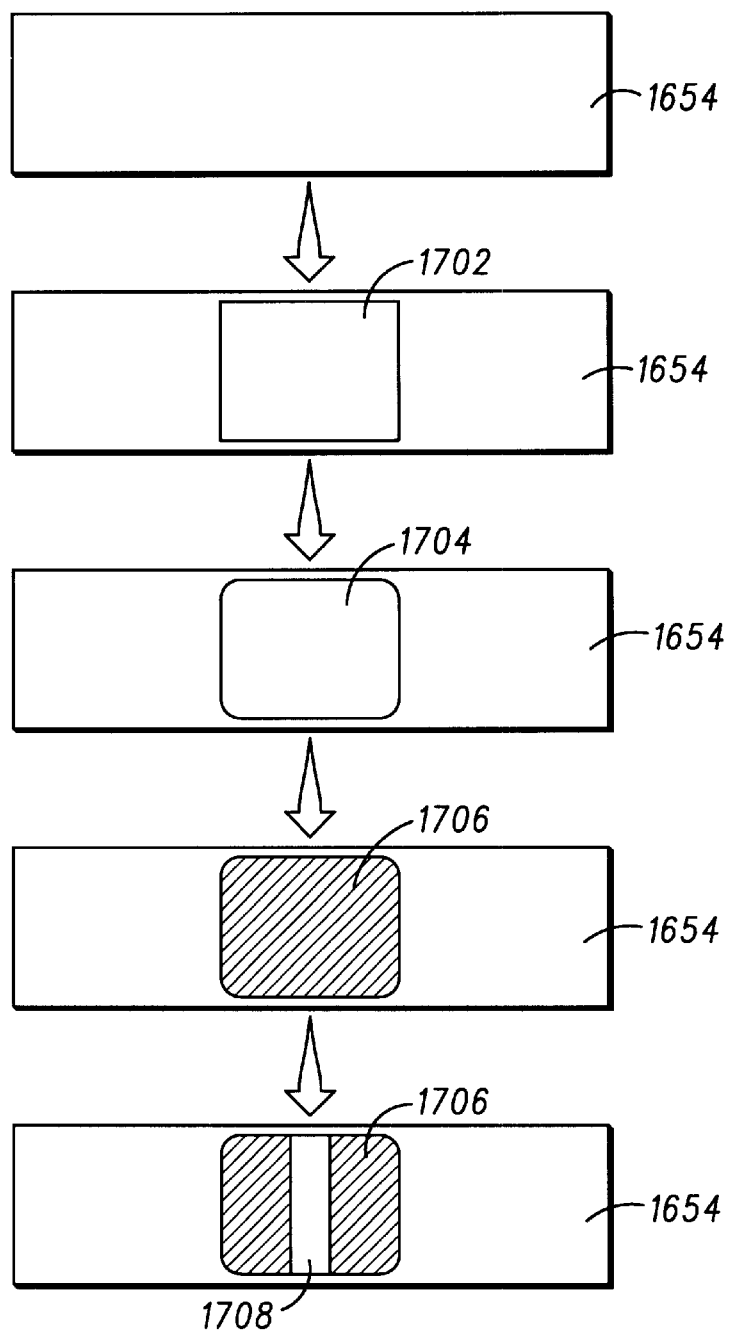
FIG. 42 is a schematic representation of the steps for making the hydrophobic region in the vertical fluid passageway of FIG. 41, in accordance with an embodiment of the present invention.

The method of forming hydrophobic region 1668 is shown schematically in FIG. 42. Initially, an oversized via 1702 is formed in green-sheet layer 1654. Via 1702 is filled, such as by screen printing, with a thick-film paste 1704. Thick-film paste 1704 contains particles of a hydrophobic glass-ceramic material dispersed in a precursor binder. The precursor binder may be polymerized, either thermally, by the application of a temperature in the range of 60 to 75° C., or by exposure to UV light. Preferably, the precursor binder contains acrylic co-monomers. The polymerization of the precursor binder solidifies the thick-film paste to provide a hydrophobic plug 1706 within green-sheet layer 1654. A via 1708 is then formed through hydrophobic plug 1706. Layer 1654 is then laminated with the other layers and fired. As a result of firing, hydrophobic plug 1706 becomes hydrophobic region 1668 sintered to layer 1654, and via 1708 defines part of vertical channel 1664.

It is to be understood that the several views of the multilayered microfluidic devices of the present invention provided herein are intended to illustrate individually certain components that may be included in a working device. Accordingly, the multilayered microfluidic devices of the present invention may include various combinations and arrangements of the basic components shown herein, depending on the particular applications of the device.

Moreover, although various embodiments have been shown and described herein, it should be understood that various modifications and substitutions, as well as rearrangements and combinations of the preceding embodiments, can be made by those skilled in the art, without departing from the novel spirit and scope of this invention.

We claim:

1. A substantially monolithic microfluidic device comprising:

(a) a substantially monolithic ceramic body, wherein said monolithic ceramic body defines a cavity, an inlet passage to said cavity, and an outlet passage from said cavity; and (b) a microwave heater integrated into said substantially monolithic ceramic body.

2. The device according to claim 1, further comprising a heat sink, wherein said heat sink is integrated into said substantially monolithic ceramic body.

3. The device according to claim 2, wherein said heat sink is a thermoelectric cooler.

4. The device according to claim 1, further comprising a plurality of cavities.

5. The device according to claim 4, wherein said plurality of cavities are substantially thermally isolated from each other.

6. The device according to claim 1 further comprising a pump, wherein said pump is integrated into said substantially monolithic ceramic body.

7. The device according to claim 6, wherein said pump is selected from the group consisting of electroosmotic pumps, electrohydrodynamic pumps, and magnetic bead pumps.

8. The device according to claim 1, wherein said substantially monolithic ceramic body has a window into said cavity.

9. The device according to claim 1, further comprising a valve in said cavity, said inlet passage to said cavity, said outlet passage from said cavity, or any combination thereof.

10. The device according to claim 1 further comprising a substantially integrated means for generating a magnetic field.

11. The device according to claim 1 further comprising a sensor selected from the group consisting of a temperature sensor, a pH sensor, and a fluid sensor.

12. The device according to claim 1 further comprising a temperature sensor, wherein said temperature sensor is integrated into said substantially monolithic ceramic body.

13. The device according to claim 12, wherein said temperature sensor is selected from the group consisting of an inductive sensor and a resistive sensor.

* * * * *